United States Patent [19]

Sohda et al.

[11] Patent Number: 5,723,479
[45] Date of Patent: Mar. 3, 1998

[54] BENZOFURAN COMPOUNDS AND THEIR USE

[75] Inventors: Takashi Sohda, Takatsuki; Hiroyuki Odaka, Kobe; Yu Momose, Takarazuka, all of Japan

[73] Assignee: Takeda Chemical Industries, Ltd., Osaka, Japan

[21] Appl. No.: 615,084

[22] Filed: Mar. 14, 1996

[30] Foreign Application Priority Data

Mar. 14, 1995 [JP] Japan ................. 7-054214

[51] Int. Cl.⁶ .................. C07D 417/12; A61K 31/40
[52] U.S. Cl. .................. 514/369; 514/374; 514/376; 548/183; 548/226; 548/235
[58] Field of Search .................. 548/183, 226, 548/235; 514/369, 374, 376

[56] References Cited

U.S. PATENT DOCUMENTS

| | | | |
|---|---|---|---|
| 4,455,427 | 6/1984 | Johnson, II | 546/269 |
| 4,495,357 | 1/1985 | Johnson | 546/269 |
| 4,738,972 | 4/1988 | Essler | 514/315 |
| 5,401,761 | 3/1995 | Goldstein | 514/369 |

FOREIGN PATENT DOCUMENTS

| | | |
|---|---|---|
| 0 428 312 | 5/1991 | European Pat. Off. |
| 0 559 571 | 9/1993 | European Pat. Off. |
| 0 604 983 | 7/1994 | European Pat. Off. |
| 0 612 743 | 8/1994 | European Pat. Off. |
| 0 629 624 | 12/1994 | European Pat. Off. |
| 0 643 050 | 3/1995 | European Pat. Off. |
| WO93/00343 | 1/1993 | WIPO . |
| WO94/29290 | 12/1994 | WIPO . |
| WO95/31454 | 11/1995 | WIPO . |

OTHER PUBLICATIONS

Dow et al., Journal of Medicinal Chemistry, vol. 34, pp. 1538–1544 (1991).

*Primary Examiner*—Robert Gerstl
*Attorney, Agent, or Firm*—Wenderoth, Lind & Ponack

[57] ABSTRACT

Benzofuran compound represented by the formula:

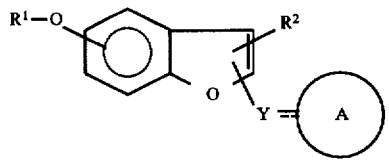

wherein

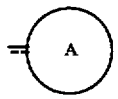

represents a group capable of releasing a cation in which ....... represents a single or double bond: $R^1$ represents an optionally substituted heterocyclic residue which may be attached to the oxygen atom through a carbon chain; $R^2$ represents a hydrogen atom, a halogen atom, an optionally substituted hydrocarbon residue, an optionally protected hydroxyl group or an optionally protected amino group; Y represents a di- or tri-valent aliphatic hydrocarbon residue having 1 to 8 carbon atoms; and the benzene ring of the benzofuran moiety may have further substituents; or a salt thereof, which has excellent hypoglycemic and hypolipidemic action.

17 Claims, No Drawings

BENZOFURAN COMPOUNDS AND THEIR USE

FIELD OF THE INVENTION

The present invention relates to new benzofuran compounds possessing hypoglycemic and hypolipidemic activity and a therapeutic agent for treating diabetes mellitus comprising such compounds.

BACKGROUND OF THE INVENTION

Traditionally, various biguanide compounds and sulfonylurea compounds have been used as therapeutic agents for diabetes mellitus. However, biguanide compounds are hardly used at present, since they cause lactic acidosis, while sulfonylurea compounds, with their potent hypoglycemic action, often cause severe hypoglycemia, requiring special attention in use. There are tetrazole, 2,4-oxazolidinedione and 2,4-thiazolidinedione derivatives known to possess hypoglycemic and hypolipidemic activity free of such drawbacks.

Tetrazole derivatives are described in, for example, the Journal of Medicinal Chemistry, Vol. 35, p. 944 (1992), U.S. Pat. No. 4,845,231 (1989), and EP 604,983-A1 (1993); 2,4-oxazolidinedione derivatives are described in, for example, Japanese Patent Unexamined Publication No. 170478/1991 and WO 9202520-A1; and 2,4-thiazolidinedione derivatives are described in, for example, Japanese Patent Unexamined Publication Nos. 85372/1986, 13088/1989, 272573/1989, 272574/1989, 167225/1990, 90078/1991, 157522/1993, 80667/1994, 213913/1993 and 9629/1994, WO 9422857, EP 604,983-A1, and Japanese Patent Unexamined Publication Nos. 2173/1991, 66579/1992 and 69383/1992.

SUMMARY OF THE INVENTION

The present inventors investigated various 5-membered heterocyclic derivatives, such as tetrazole, 2,4-oxazolidinedione and 2,4-thiazolidinedione, and found that new derivatives having a benzofuran ring on the 5-position substituent possess hypoglycemic and hypolipidemic activity. The present inventors made further investigations based on this finding, and developed the present invention.

More specifically, the present invention provides benzofuran compounds represented by the formula:

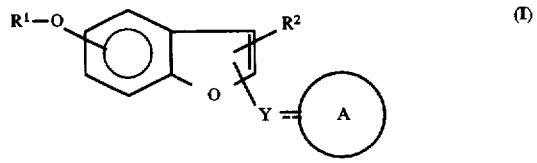

wherein

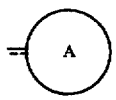

represents a group capable of releasing a cation in which ——— represents a single or double bond; $R^1$ represents an optionally substituted heterocyclic residue which may be attached to the oxygen atom through a carbon chain; $R^2$ represents a hydrogen atom, a halogen atom, an optionally substituted hydrocarbon residue, an optionally protected hydroxyl group or an optionally protected amino group; Y represents a di- or tri-valent aliphatic hydrocarbon residue having 1 to 8 carbon atoms; the benzene ring of the benzofuran moiety may have further substituents; or a salt thereof, and a pharmaceutical composition comprising as an active ingredient a benzofuran compound represented by the formula (I) or a pharmaceutically acceptable salt thereof.

With respect to the above formula (I), the group represented by

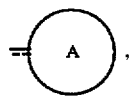

which is capable of releasing a cation, includes groups which are capable of releasing a cation or which are convertible thereinto either chemically (e.g., chemical reaction such as oxidation, reduction and hydrolysis) or biologically, i.e., under physiological conditions (e.g., in vivo reaction such as oxidation, reduction and hydrolysis, which is catalyzed by in vivo enzymes).

The group capable of releasing a cation is exemplified by (1) 5-membered heterocyclic groups capable of releasing a cation, (2) cyano group, (3) carboxyl group, (4) $C_{2-7}$ alkoxycarbonyl groups (e.g., methoxycarbonyl, ethoxycarbonyl), (5) $C_{7-11}$ aryloxycarbonyl groups (e.g., phenyloxycarbonyl, naphthyloxycarbonyl), (6) 5- or 6-membered heterocyclic-oxycarbonyl groups containing 1 to 4 hetero atoms selected from N, O and S in addition to carbon atoms (e.g., pyridyloxycarbonyl, thienyloxycarbonyl), (7) sulfonic acid group, (8) sulfamoyl group which is optionally mono-substituted by $C_{1-4}$ alkyl groups (e.g., methyl, ethyl, propyl, butyl, isobutyl, tert-butyl), (9) phosphonic acid group,

(10) di-$C_{1-4}$ alkoxyphosphoryl groups (e.g., dimethoxyphosphoryl, diethoxyphosphoryl, dipropoxyphosphoryl),

(11) carbamoyl group which is optionally mono-substituted by $C_{1-4}$ alkyl groups (e.g., methyl, ethyl, propyl, butyl, isobutyl, tert-butyl),

(12) $C_{2-7}$ alkyl sulfonylthiocarbamoyl groups (e.g., methylsulfonylthiocarbamoyl, ethylsulfonylthiocarbamoyl), and

(13) trifluoromethanesulfonamide (—$NHSO_2CF_3$).

The 5-membered heterocyclic groups are exemplified by rings containing 1 to 4 atoms selected from N, O and S as ring component atoms, such as the following:

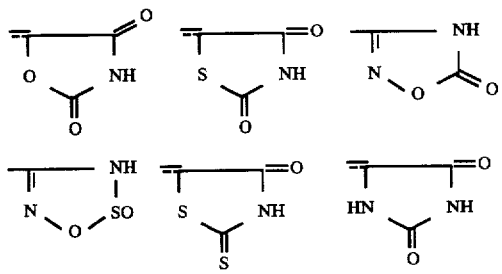

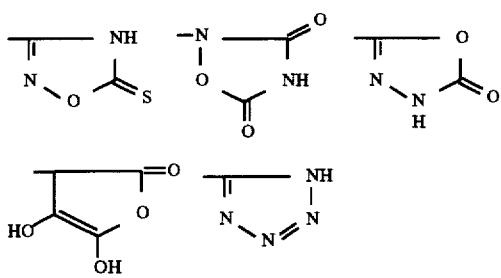

The group capable of releasing a cation is preferably a 5-membered heterocyclic group capable of releasing a cation. More preferred are groups represented by the formula:

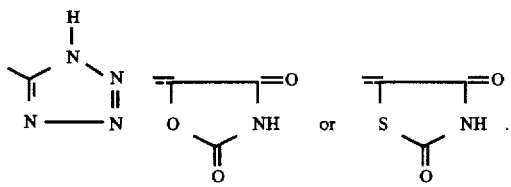

The group capable of releasing a cation is most preferably a group represented by the formula:

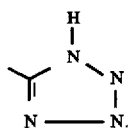

The optionally substituted heterocyclic residue represented by $R^1$ may be attached directly to —O— or to —O— through a carbon chain, preferably through a carbon chain. The chain may be straight-chain or branched, and may be saturated or unsaturated. The chain is preferably a divalent hydrocarbon having 1 to 8 carbon atoms, more preferably one having 1 to 4 carbon atoms.

The heterocyclic residue is exemplified by a 5- or 6-membered ring or a condensed ring containing at least one nitrogen atom as a ring component atom. The heterocyclic residue is preferably an aromatic ring having an unsaturated bond. It may have two or more nitrogen atoms as ring component atoms and it may contain hetero atoms such as an oxygen atom and a sulfur atom in addition to nitrogen atoms. This heterocyclic residue is exemplified by pyrrolyl (2-pyrrolyl), pyrazolyl (3-pyrazolyl), imidazolyl (2-imidazolyl, 4-imidazolyl), triazolyl (1,2,3-triazol-4-yl, 1,2,4-triazol-3-yl), tetrazolyl, oxazolyl (2-oxazolyl, 4-oxazolyl) and thiazolyl (2-thiazolyl, 4-thiazolyl).

These heterocyclic residues may have one or more substituents at any positions on the ring thereof. Such substituents are exemplified by hydrocarbon residues, heterocyclic groups and amino groups; these may have further substituents.

Examples of the hydrocarbon residues include aliphatic hydrocarbon residues, alicyclic hydrocarbon residues, alicyclic-aliphatic hydrocarbon residues, aromatic aliphatic hydrocarbon residues and aromatic hydrocarbon residues.

Such aliphatic hydrocarbon residues are exemplified by those having 1 to 8 carbon atoms. Examples of the aliphatic hydrocarbon residues include saturated aliphatic hydrocarbon residues (e.g., alkyl groups) having 1 to 8 carbon atoms, preferably 1 to 4 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl and octyl; and unsaturated aliphatic hydrocarbon residues (e.g., alkenyl groups, alkadienyl groups, alkynyl groups, alkadiynyl groups) having 2 to 8 carbon atoms, preferably 2 to 4 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl.

Such alicyclic hydrocarbon residues are exemplified by those having 3 to 7 carbon atoms. Examples of the alicyclic hydrocarbon residues include saturated alicyclic hydrocarbon residues (e.g., cycloalkyl groups) having 3 to 7 carbon atoms, preferably 5 or 6 carbon atoms, such as cyclopropyl, cyclobutyl, cyclopentyl, cyclohexyl and cycloheptyl; and unsaturated alicyclic hydrocarbon residues (e.g., cycloalkenyl groups, cycloalkadienyl groups) having 5 to 7 carbon atoms, preferably 5 or 6 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl.

Such alicyclic-aliphatic hydrocarbon residues are exemplified by those resulting from binding of the above-mentioned alicyclic hydrocarbon residues and above-mentioned aliphatic hydrocarbon residues to have 4 to 9 carbon atoms. Examples of the alicyclic-aliphatic hydrocarbon residues include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl.

Such aromatic aliphatic hydrocarbon residues are exemplified by those having 7 to 13 carbon atoms. Examples of the aromatic aliphatic hydrocarbon residues include phenylalkyls having 7 to 9 carbon atoms, such as benzyl, phenethyl, 1-phenylethyl, 3-phenylpropyl, 2-phenylpropyl and 1-phenylpropyl; and naphthylalkyls having 11 to 13 carbon atoms such as α-naphthylmethyl, α-naphthylethyl, β-naphthylmethyl and β-naphthylethyl.

Such aromatic hydrocarbon residues are exemplified by those having 6 to 14 carbon atoms. Examples of the aromatic hydrocarbon residues include phenyl and naphthyl (α-naphthyl, β-naphthyl).

The above-described heterocyclic group as a substituent is a 5- or 6-membered ring group containing as ring component atoms 1 to 3 atoms selected from N, O and S in addition to carbon atoms, and which is attached through carbon. Examples of the heterocyclic groups include unsaturated heterocyclic groups such as thienyl (2-thienyl, 3-thienyl), furyl (2-furyl, 3-furyl), pyridyl (2-pyridyl, 3-pyridyl, 4-pyridyl), thiazolyl (2-thiazolyl, 4-thiazolyl, 5-thiazolyl), oxazolyl (2-oxazolyl, 4-oxazolyl, 5-oxazolyl), imidazolyl (2-imidazolyl, 4-imidazolyl, 5-imidazolyl), pyrimidinyl (2-pyrimidinyl, 4-pyrimidinyl, 5-pyrimidinyl, 6-pyrimidinyl), pyrazinyl, and pyridazinyl (3-pyridazinyl, 4-pyridazinyl, 5-pyridazinyl, 6-pyridazinyl); and saturated heterocyclic groups such as piperidinyl (2-piperidinyl, 3-piperidinyl, 4-piperidinyl), pyrrolidinyl (2-pyrrolidinyl, 3-pyrrolidinyl), morpholinyl (2-morpholinyl, 3-morpholinyl) and tetrahydrofuryl (2-tetrahydrofuryl, 3-tetrahydrofuryl).

The above-described amino group may be substituted; substituted amino groups include N-mono-substituted and N,N-di-substituted amino groups.

The "N-mono-substituted amino group" is an amino group having one substituent. Said substituent is exemplified by lower alkyl groups (e.g., those having 1 to 4 carbon atoms, such as methyl, ethyl, propyl, butyl, isobutyl and tert-butyl), cycloalkyl groups (e.g., those having 3 to 7 carbon atoms, such as cyclopentyl and cyclohexyl), aryl groups (e.g., those having 6 to 14 carbon atoms, such as phenyl and naphthyl), aromatic heterocyclic groups (e.g., pyridyl, thienyl, furyl, oxazolyl, thiazolyl), non-aromatic heterocyclic groups (e.g., piperidinyl, pyrrolidinyl, morpholinyl), aralkyl groups (e.g., those having 7 to 13 carbon atoms, such as benzyl and phenethyl), acyl groups (e.g., those having 1 to 6 carbon atoms, such as alkanoyl groups such as acetyl and propionyl), carbamoyl groups, N-mono-substituted carbamoyl groups (e.g., N-methylcarbamoyl, N-ethylcarbamoyl, N-propylcarbamoyl), N,N-di-substituted carbamoyl groups (e.g., N,N-dimethylcarbamoyl, N-methyl-N-ethylcarbamoyl, N,N-diethylcarbamoyl), lower alkoxycarbonyl groups (e.g., those having 2 to 5 carbon atoms, such as methoxycarbonyl, ethoxycarbonyl and propoxycarbonyl), hydroxyl groups, lower alkoxy groups (e.g., those having 1 to 4 carbon atoms, such as methoxy, ethoxy, propoxy and butoxy), and aralkyloxy groups (e.g., those having 7 to 13 carbon atoms, such as benzyloxy, phenethyloxy and naphthylmethyloxy).

The "N,N-di-substituted amino group" is an amino group having two substituents, one of said substituents being exemplified by the same substituents as those for the above-described "N-mono-substituted amino group," the other being exemplified by lower alkyl groups (e.g., those having 1 to 4 carbon atoms, such as methyl, ethyl, propyl, butyl, isobutyl and tert-butyl), cycloalkyl groups (e.g., those having 3 to 7 carbon atoms, such as cyclopropyl, cyclobutyl, cyclopentyl, cyclohexyl and cycloheptyl), aryl groups (e.g., those having 6 to 14 carbon atoms, such as phenyl and naphthyl) and aralkyl groups (e.g., those having 7 to 13 carbon atoms, such as benzyl and phenethyl). The two substituents may form a cyclic amino group in cooperation with a nitrogen atom. Such cyclic amino groups include 1-azetidinyl, pyrrolidino, piperidino, morpholino, piperazino, and piperazino having at 4-position a lower alkyl group (e.g., one having 1 to 4 carbon atoms, such as methyl, ethyl and propyl), an aralkyl group (e.g., those having 7 to 13 carbon atoms, such as benzyl, phenethyl and naphthylmethyl), an aryl group (e.g., those having 6 to 14 carbon atoms, such as phenyl, 4-methylphenyl, naphthyl), or the like.

The hydrocarbon residue or heterocyclic group as a substituent on the optionally substituted heterocyclic residue for $R^1$, which may be attached through a carbon chain, may have substituents at any positions on the ring thereof. When the hydrocarbon residue contains an alicyclic group (i.e., when the hydrocarbon residue is an aliphatic hydrocarbon residue, an alicyclic-aliphatic hydrocarbon residue or an aromatic aliphatic hydrocarbon residue), or when the heterocyclic group is saturated, it may have 1 to 3 lower alkyl groups having 1 to 3 carbon atoms (e.g., methyl, ethyl, propyl, isopropyl) on the ring thereof (an N atom contained). When the hydrocarbon residue contains an aromatic hydrocarbon residue (i.e., when the hydrocarbon residue is an aromatic aliphatic hydrocarbon residue or an aromatic hydrocarbon residue) or when the heterocyclic group is unsaturated, it may have 1 to 4 substituents, which may be the same or different, on the ring thereof. Examples of the substituents include halogens (e.g., fluorine, chlorine, iodine), hydroxy, cyano, nitro, trifluoromethyl, lower alkoxy groups (e.g., those having 1 to 4 carbon atoms such as methoxy, ethoxy, propoxy, isopropoxy and butoxy), lower alkyl groups (e.g., those having 1 to 4 carbon atoms such as methyl, ethyl, propyl, isopropyl and butyl), lower alkoxycarbonyl groups (e.g., those having 2 to 4 carbon atoms such as methoxycarbonyl, ethoxycarbonyl and propoxycarbonyl), lower alkylthio groups (e.g., those having 1 to 3 carbon atoms such as methylthio, ethylthio, propylthio and isopropylthio) and lower alkylamino groups (e.g., those having 1 to 4 carbon atoms such as methylamino, ethylamino and dimethylamino).

When the optionally substituted heterocyclic residue represented by $R^1$, which may be attached through a carbon chain, has two or more hydrocarbon residues as substituents therefor, which hydrocarbon residues are located at mutually adjacent positions on the heterocyclic ring, these residues may be linked together to form a condensed ring. This means that the two hydrocarbon residues are linked together to form a saturated or unsaturated di-valent chain hydrocarbon residue having 3 to 5 carbon atoms. Examples of the chain hydrocarbon residues include $-CH_2CH_2CH_2-$, $-CH_2CH_2CH_2CH_2-$, $-CH_2CH_2CH_2CH_2CH_2-$, $-CH=CHCH_2-$, $-CH=CH-CH=CH-$, $-CH=CH-CH=CH-CH_2-$ and $-CH=CH-CH_2CH_2CH_2-$.

Of the optionally substituted heterocyclic residues represented by $R^1$, which may be attached through a carbon chain, preference is given to the ring represented by the formula:

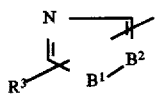

wherein $B^1$ represents a sulfur atom, an oxygen atom or $NR^4$ [$R^4$ represents a hydrogen atom, a lower alkyl group or an aralkyl group]; $B^2$ represents a nitrogen atom or $C-R^5$ ($R^5$ represents a hydrogen atom or an optionally substituted hydrocarbon residue or heterocyclic group); $R^3$ represents a hydrogen atom or an optionally substituted hydrocarbon residue or heterocyclic group; when $R^3$ and $R^5$ are attached to the adjacent carbon atoms, $R^3$ and $R^5$ may be linked together to form a condensed ring.

Examples of the lower alkyl group for $R^4$ include those having 1 to 3 carbon atoms, such as methyl and ethyl.

Examples of the aralkyl group for $R^4$ include those having 7 to 13 carbon atoms such as benzyl and phenethyl.

In the optionally substituted hydrocarbon residue or heterocyclic group represented by $R^3$ or $R^5$, the hydrocarbon residue, the heterocyclic group and substituents for these groups, are similar to those mentioned above as substituents for the heterocyclic residue in $R^1$. The condensed ring formed by $R^3$ and $R^5$ linked together is similar to the condensed ring formed by the heterocyclic group in $R^1$ having two substituent hydrocarbon residues at mutually adjacent positions.

Although this heterocyclic residue is attached through a possible atom on the ring thereof, it is preferably a group attached through a carbon atom adjacent to a nitrogen atom. An example of a preferred group is a group attached through $B^2$, when $B^1$ is $NR^4$ and $B^2$ is $C-R^5$.

Of the heterocyclic groups represented by the above formula, preference is given to the thiazolyl or oxazolyl represented by the formula:

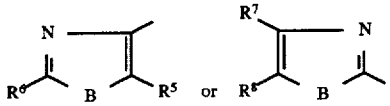

wherein $R^5$ has the same definition as above; $R^6$, $R^7$ and $R^8$, which may be the same or different, represent a hydrogen atom or an optionally substituted hydrocarbon residue or heterocyclic group; $R^7$ and $R^8$ may be linked together to form a condensed ring; B represents an oxygen atom or a sulfur atom.

In the optionally substituted hydrocarbon residue or heterocyclic group represented by $R^6$, $R^7$ or $R^8$, the hydrocarbon residue, the heterocyclic group and substituents for these groups, are similar to those mentioned above as substituents for the heterocyclic residue in $R^1$. These $R^7$ and $R^8$ substituents may be linked together to form a condensed ring. In this case as well, the condensed ring is similar to the condensed ring formed by the heterocyclic residue in $R^1$ having two substituent hydrocarbon residues at mutually adjacent positions.

With respect to the above formula (i), $R^2$ represents hydrogen, halogen atom, an optionally substituted hydrocarbon residue, an optionally protected hydroxyl group or an optionally protected amino group.

Examples of the halogen atom include fluorine, chlorine and iodine.

The hydrocarbon residue and substituents therefor in the optionally substituted hydrocarbon residue are similar to those mentioned above as substituents for the heterocyclic residue in $R^1$.

The protecting group in the optionally protected hydroxyl group is exemplified by (1) $C_{1-6}$ alkyl groups (e.g., methyl, ethyl, propyl, isopropyl, butyl, isobutyl, sec-butyl, tert-butyl), (2) $C_{6-14}$ aryl groups (e.g., phenyl, naphtyl), (3) $C_{7-13}$ aralkyl groups (e.g., benzyl, phenethyl, naphthylmethyl), (4) formyl.

(5) $C_{2-7}$ alkylcarbonyl groups (e.g., acetyl, propionyl, butyryl, valeryl), (6) $C_{7-11}$ aryloxycarbonyl groups (e.g., phenyloxycarbonyl, naphthyloxycarbonyl), (7) $C_{7-11}$ arylcarbonyl groups (e.g., benzoyl, naphthoyl), (8) $C_{8-14}$ aralkylcarbonyl groups (e.g., benzylcarbonyl, phenethylcarbonyl), (9) pyranyl or furanyl, and

(10) tri-$C_{1-4}$ alkylsilyl groups (e.g., trimethylsilyl, triethylsilyl).

These protecting groups may have 1 to 4 substituents at any possible position. Examples of the substituents include halogen atom (e.g., chlorine, iodine, fluorine), $C_{1-6}$ alkyl groups (e.g., methyl, ethyl, propyl, isopropyl, butyl, isobutyl, sec-butyl, tert-butyl), $C_{6-14}$ aryl groups (e.g., phenyl, naphthyl), $C_{7-13}$ aralkyl groups (e.g., benzyl, phenethyl, naphthylmethyl) and nitro group.

The protecting group in the optionally protected amino group is exemplified by (1) formyl, (2) $C_{2-7}$ alkylcarbonyl groups (e.g., acetyl, propionyl, butyryl, valeryl), (3) $C_{7-11}$ arylcarbonyl groups (e.g., benzoyl, naphthoyl), (4) $C_{2-7}$ alkyloxycarbonyl groups (e.g., methoxycarbonyl, ethoxycarbonyl), (5) $C_{7-11}$ aryloxycarbonyl groups (e.g., phenyloxycarbonyl, naphthyloxycarbonyl), (6) $C_{8-14}$ aralkylcarbonyl (e.g., benzylcarbonyl, phenethylcarbonyl), (7) trityl group, and (8) phthaloyl group.

These protecting groups may have 1 to 3 substituents at any possible position. Examples of the substituents include halogen atom (e.g., chlorine, iodine, fluorine), $C_{2-7}$ alkylcarbonyl groups (e.g., acetyl, propionyl, butyryl, valeryl) and nitro group.

With respect to the formula (I), $R^2$ is most preferably hydrogen.

The di- or tri-valent aliphatic hydrocarbon residue having 1 to 8 carbon atoms represented by Y may be straight-chain or branched, and may be saturated or unsaturated, it preferably has 1 to 7 carbon atoms. Specifically, the di-valent aliphatic hydrocarbon residue is exemplified by saturated ones such as —$CH_2$—, —$CH(CH_3)$—, —$(CH_2)_2$—, —$CH(C_2H_5)$—, —$(CH_2)_3$—, —$(CH_2)_4$—, —$(CH_2)_5$—, —$(CH_2)_6$— and —$(CH_2)_7$—, and unsaturated ones such as —CH=CH—, —C($CH_3$)=CH—, —CH=CH—$CH_2$—, —C($C_2H_5$)=CH—, —$CH_2$—CH=CH—$CH_2$—, —$CH_2$—$CH_2$—CH=CH—$CH_2$—, —CH=CH—CH=CH—$CH_2$— and —CH=CH—CH=CH—CH=CH—$CH_2$—. The tri-valent aliphatic hydrocarbon residue is exemplified by saturated ones such as —CH=, —C($CH_3$)=, —$CH_2$CH=, —C($C_2H_5$)=, —$(CH_2)_2$—CH=, —$(CH_2)_3$—CH=, —$(CH_2)_4$CH=, —$(CH_2)_5$—CH= and —$(CH_2)_6$—CH=; and unsaturated ones such as —CH=CH—CH=, —CH($C_2H_5$)—CH=, —$CH_2$—CH=CH—CH=, —$CH_2$—$CH_2$—CH=CH—CH=, —CH=CH—CH=CH—CH= and —CH=CH—CH=CH—CH=CH—CH=. Saturated aliphatic hydrocarbon residues having 2 to 5 carbon atoms are more preferable, —$CH_2CH_2CH_2$— being most preferable.

With respect to the formula (I), the benzene ring in the benzofuran ring may have 1 to 3 substituents. Examples of the substituents include halogen atom (e.g., fluorine, chlorine, iodine), hydroxyl group, cyano group, nitro group, trifluoromethyl group, lower alkoxy groups (e.g., those having 1 to 4 carbon atoms, such as methoxy, ethoxy, propoxy, isopropoxy and butoxy), lower alkyl groups (e.g., those having 1 to 4 carbon atoms, such as methyl, ethyl, propyl, isopropyl and butyl), lower alkoxycarbonyl groups (e.g., those having 2 to 4 carbon atoms, such as methoxycarbonyl, ethoxycarbonyl and propoxycarbonyl), lower alkylthio groups (e.g., those having 1 to 3 carbon atoms, such as methylthio, ethylthio, propylthio and isopropylthio) and lower alkylamino groups (e.g., those having 1 to 4 carbon atoms, such as methylamino, ethylamino and dimethylamino).

The benzene ring in the benzofuran ring is preferably unsubstituted.

With respect to the formula (I), Y and $R^2$ are attached to 2-, or 3-position on the benzofuran ring, $R^1$-O is attached to 4-, 5-, 6- or 7-position on the benzofuran ring.

$R^1$-O is preferably attached to 6-position on the benzofuran ring and Y is preferably attached to 2-position on the benzofuran ring.

Preferable examples of the compounds represented by the formula (I) include those of the formula (I) in which $R^1$ is oxazole group which is optionally substituted by phenyl and/or methyl, and which is attached through methylene group; the partial formula

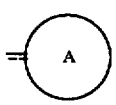

represents

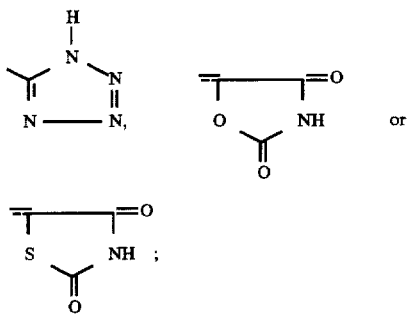

$R^2$ is hydrogen;

Y is di- or tri-valent aliphatic hydrocarbon residue having 1 to 4 carbon atoms; $R^1$-O is attached to 6-position and Y is attached to 2-position on the benzofuran ring.

Preferable specific examples of the compounds represented by the formula (I) include 5-[2-[6-(5-methyl-2-phenyl-4-oxazolylmethoxy)-2-benzofuranyl]ethyl]-1H-tetrazole;

5-[3-[6-(5-methyl-2-phenyl-4-oxazolylmethoxy)-2-benzofuranyl]propyl]-1H-tetrazole;

5-[4-[6-(5-methyl-2-phenyl-4-oxazolylmethoxy)-2-benzofuranyl]butyl]-1H-tetrazole;

5-[6-(5-methyl-2-phenyl-4-oxazolylmethoxy)-2-benzofuranylmethylidene]-2,4-thiazolidinedione;

5-[6-(5-methyl-2-phenyl-4-oxazolylmethoxy)-2-benzofuranylmethyl]-2,4-thiazolidinedione;

5-[3-[6-(5-methyl-2-phenyl-4-oxazolylmethoxy)-2-benzofuranyl]propyl]-2,4-thiazolidinedione;

5-[6-(5-methyl-2-phenyl-4-oxazolylmethoxy)-2-benzofuranylmethyl]-2,4-oxazolidinedione;

5-[3-[6-(5-methyl-2-phenyl-4-oxazolylmethoxy)-2-benzofuranyl]propyl]-2,4-oxazolidinedione; and 5-[3-[5-(5-methyl-2-phenyl-4-oxazolylmethoxy)-2-benzofuranyl]propyl]-1H-tetrazole.

Among these compounds, 5-[3-[6-(5-methyl-2-phenyl-4-oxazolylmethoxy)-2-benzofuranyl]propyl]-1H-tetrazole is especially preferable.

In the present invention, the salt of the compounds represented by the formula (I) (hereinafter referred to as compound (I)) is preferably a pharmaceutically acceptable salt, exemplified by salts with inorganic bases, salts with organic bases, salts with inorganic acids, salts with organic acids and salts with basic or acidic amino acids. Preferable examples of salts with inorganic bases include alkali metal salts such as sodium salt and potassium salt, alkaline earth metal salts such as calcium salt and magnesium salt, aluminum salt and ammonium salt. Preferable examples of salts with organic bases include salts with trimethylamine, triethylamine, pyridine, picoline, ethanolamine, diethanolamine, triethanolamine, dicyclohexylamine and N,N'-dibenzylethylenediamine. Preferable examples of salts with inorganic acids include salts with hydrochloric acid, hydrobromic acid, nitric acid, sulfuric acid and phosphoric acid. Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable examples of salts with basic amino acids include salts with arginine, lysine and ornithine. Preferable examples of salts with acidic amino acids include salts with aspartic acid and glutamic acid. Of these salts, sodium salt and potassium salt are most preferable.

Compound (I) of the present invention or a pharmaceutically acceptable salt thereof exhibits hypoglycemic and hypolipidemic action and insulin sensitivity enhancing action with low toxicity, and can be used as such or in a composition with a per se known pharmaceutically acceptable carrier, excipient, filler and other additives in mammals (e.g., humans, mice, rats, rabbits, dogs, cats, bovines, horses, swines, monkeys) as an anti-diabetic agent, an agent for enhancing insulin sensitivity, a hyperlipidemic agent or a hypotensive agent.

Compound (I) of the present invention is low in toxicity. For example, oral administration of the compound of Example 7 at a daily dose of 15 mg/kg for 4 days to mice caused no change in body weight or liver weight in comparison with control.

Concerning the method of administration, compound (I) of the present invention is normally used orally in the form of tablets, capsules (including soft capsules and microcapsules), powders, granules and other forms, but in some cases it can be non-orally administered in the form of injectable preparations, suppositories, pellets and other forms. Single dose is 0.05 to 10 mg/kg for oral administration in adults, preferably 1 to 3 times daily.

Compound (I) of the present invention can be used in formulation with a pharmaceutically acceptable carrier orally or non-orally in the form of solid preparations such as tablets, capsules, granules and powders, or liquid preparations such as syrups and injectable preparations.

Pharmaceutically acceptable carriers are various organic or inorganic carrier substances in common use as pharmaceutical materials, including excipients, lubricants, binders and disintegrating agents for solid preparations; and solvents, solubilizing agents, suspending agents, isotonizing agents, buffers and soothing agents for liquid preparations. If necessary, pharmaceutical additives such as preservatives, antioxidants, coloring agents and sweetening agents can be used.

Preferable examples of excipients include lactose, sucrose, D-mannitol, starch, crystalline cellulose and light silicic acid anhydride. Preferable examples of lubricants include magnesium stearate, calcium stearate, talc and colloidal silica. Preferable examples of binders include crystalline cellulose, sucrose, D-mannitol, dextrin, hydroxypropyl cellulose, hydroxypropylmethyl cellulose and polyvinylpyrrolidone. Preferable examples of disintegrating agents include starch, carboxymethyl cellulose, carboxymethyl cellulose calcium, crosscalmellose sodium and carboxymethyl starch sodium. Preferable examples of solvents include water for injection, alcohol, propylene glycol, macrogol, sesame oil and corn oil.

Preferable examples of solubilizing agents include polyethylene glycol, propylene glycol, D-mannitol, benzyl benzoate, ethanol, tris-aminomethane, cholesterol, triethanolamine, sodium carbonate and sodium citrate. Preferable examples of suspending agents include surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable examples of isotonizing agents include sodium chloride, glycerol and D-mannitol. Preferable examples of buffers include buffer solutions of phosphates, acetates, carbonates and citrates. Preferable examples of soothing agents include benzyl alcohol. Preferable examples of preservatives include p-oxybenzoic acid esters, chlorobutanol, benzyl alcohol, phenethyl alcohol, dehydroacetic acid and sorbic acid. Preferable examples of antioxidants include sulfites and ascorbic acid.

The method of producing the compound (I) of the present invention is described below.

The compound (I) is produced by per se known methods, such as the following methods and methods analogous thereto.

(1) Method of synthesis of compound (I-A), wherein the group capable of releasing a cation is tetrazole

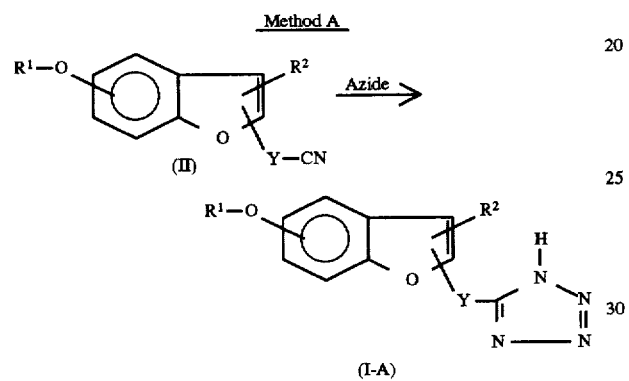

wherein the symbols have the same definitions as those given above.

Compound (I-A), wherein the group capable of releasing a cation is tetrazole, is produced by reaction of nitrile derivative (II) with an azide compound. The reaction for compound (I-A) from compound (II) is carried out by reacting with ammonium chloride and sodium azide in N,N-dimethylformamide by, for example, the method described in the Journal of American Chemical Society, Vol. 80, p. 3908 (1958). The amounts of ammonium chloride and sodium azide used are normally 1 to 7 mol, preferably 1 to 5 mol, per mol of compound (II); the reaction is carried out at 50° to 180° C. for 1 to 50 hours. The reaction for compound (I-A) from compound (II) can also be carried out by reacting compound (II) with trimethyltin azide or tributyltin azide, followed by acid treatment by the method described in the Journal of Organic Chemistry, Vol. 56, p. 2395 (1991).

Compound (I-A) thus obtained and salts thereof can be isolated and purified by known means of separation and purification such as ordinary concentration, concentration under reduced pressure, solvent extraction, crystallization, recrystallization, phasic transfer and chromatography.

(2) Methods of synthesis of compound (I-B), wherein the group capable of releasing a cation is 2,4-oxazolidinedione

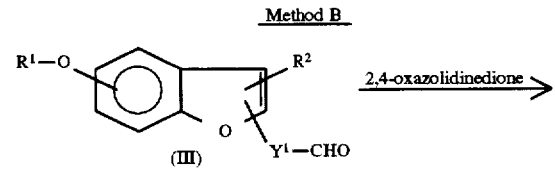

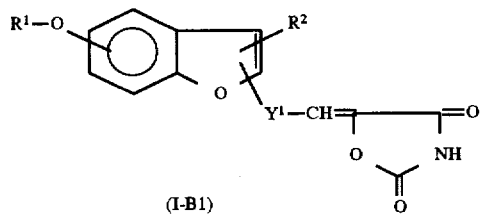

wherein $Y^1$ represents a bond or a divalent aliphatic hydrocarbon residue; the other symbols have the same definitions as those given above.

The aliphatic hydrocarbon residue represented by $Y^1$ is a divalent aliphatic hydrocarbon residue having 1 to 7 carbon atoms, selected from the di- or tri-valent aliphatic hydrocarbon residues for Y, which have 1 to 8 carbon atoms.

Compound (I-B1) is produced by condensation of aldehyde compound (III) with 2,4-oxazolidinedione. This reaction is carried out in a solvent in the presence of a base. The solvent is exemplified by alcohols such as methanol, ethanol, propanol, isopropanol and 2-methoxyethanol; aromatic hydrocarbons such as benzene, toluene and xylene; ethers such as diethyl ether, isopropyl ether and tetrahydrofuran; N,N-dimethylformamide, dimethyl sulfoxide, acetic acid and mixtures thereof. The base is exemplified by sodium alkoxides (e.g., sodium methoxide, sodium ethoxide); alkali metal salts such as potassium carbonate, sodium carbonate and sodium acetate; metal hydrides such as sodium hydride; and secondary amines such as piperidine, piperazine, pyrrolidine, morpholine, diethylamine and diisopropylamine. The amount of 2,4-oxazolidinedione used is normally 1 to 10 mol equivalents, preferably 1 to 5 mol equivalents, per mol of compound (III). The amount of base used is normally 0.01 to 5 mol equivalents, preferably 0.05 to 2 mol equivalents, per mol of compound (III). This reaction is carried out at 0° to 180° C., preferably 50° to 130° C. for 0.5 to 30 hours.

Compound (I-B1) thus obtained can be isolated and purified by known means of separation and purification such as ordinary concentration, concentration under reduced pressure, solvent extraction, crystallization, recrystallization, phasic transfer and chromatography, and may be obtained as a mixture of the (E)- and (Z)-configurations in terms of the double bond at the 5-position in the 2,4-oxazolidinedione ring.

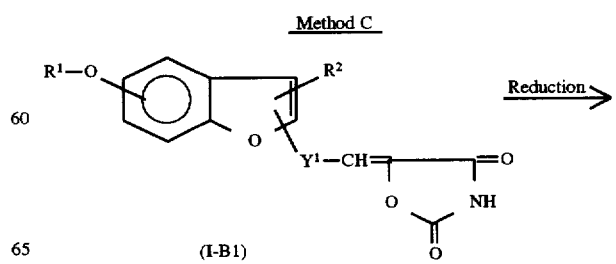

-continued
Method C

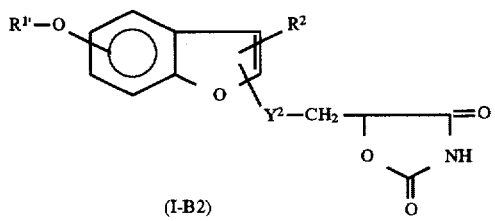

(I-B2)

wherein $R^{1''}$ represents an optionally substituted heterocyclic residue which may be attached through a carbon chain; $Y^2$ represents a bond or a divalent saturated aliphatic hydrocarbon residue; the other symbols have the same definitions as those given above. The saturated aliphatic hydrocarbon residue represented by $Y^2$ is a saturated one selected from the divalent aliphatic hydrocarbon residues for $Y^1$, which have 1 to 7 carbon atoms.

The optionally substituted heterocyclic residue for $R^{1''}$ which may be attached through a carbon chain is one having a saturated carbon chain selected from the optionally substituted heterocyclic residues for $R^1$ which may be attached through a carbon chain.

Compound (I-B2) can be produced by subjecting compound (I-B1) to a reducing reaction. This reduction is carried out in a solvent in the presence of a catalyst in a hydrogen atmosphere of 1 to 150 atm by a conventional method. The solvent is exemplified by alcohols such as methanol, ethanol, propanol, isopropanol and 2-methoxyethanol; aromatic hydrocarbons such as benzene, toluene and xylene; ethers such as diethyl ether, isopropyl ether and tetrahydrofuran; halogenated hydrocarbons such as chloroform, dichloromethane and 1,1,2,2-tetrachloroethane; ethyl acetate, acetic acid, N,N-dimethylformamide and mixtures thereof. The reaction is facilitated by the use of a catalyst exemplified by metals such as nickel compounds, and transition metal catalysts such as palladium, platinum and rhodium. Reaction temperature is normally 0° to 100° C., preferably 10° to 80° C., reaction time being 0.5 to 50 hours.

Compound (I-B2) thus obtained can be isolated and purified by known means of separation and purification such as ordinary concentration, concentration under reduced pressure, solvent extraction, crystallization, recrystallization, phasic transfer and chromatography.

(3) Methods of synthesis of compound (I-C), wherein the group capable of releasing a cation is 2,4-thiazolidinedione

Method D

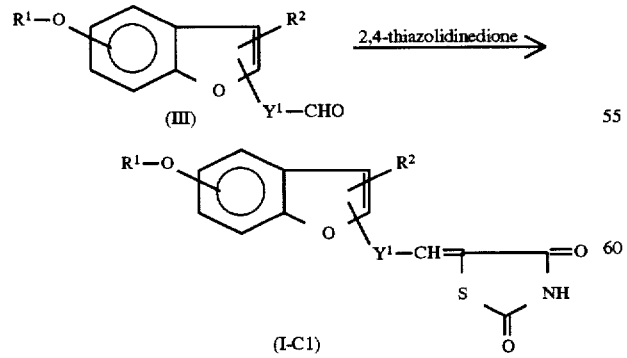

wherein the symbols have the same definitions as those given above.

Compound (I-C1) is produced by condensation of aldehyde compound (III) with 2,4-thiazolidinedione. This reaction is carried out in the same manner as method B.

Compound (I-C1) thus obtained can be isolated and purified by known means of separation and purification such as ordinary concentration, concentration under reduced pressure, solvent extraction, crystallization, recrystallization, phasic transfer and chromatography, and may be obtained as a mixture of the (E)- and (Z)-configurations, in terms of the double bond at the 5-position in the 2,4-thiazolidinedione ring.

Method E

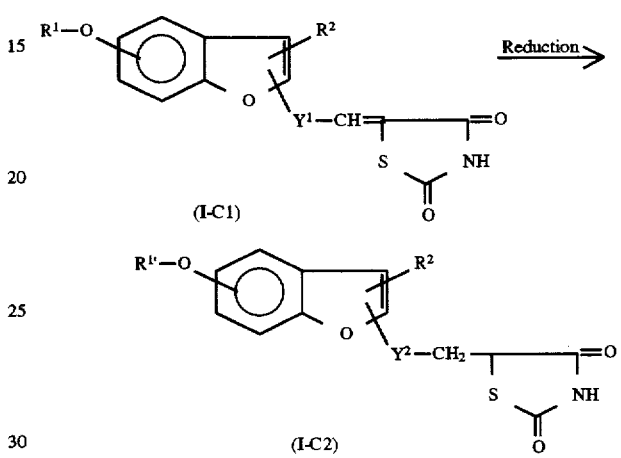

wherein the symbols have the same definitions as those given above.

This reaction is carried out in the same manner as method C.

Compound (I-C2) thus obtained can be isolated and purified by known means of separation and purification such as ordinary concentration, concentration under reduced pressure, solvent extraction, crystallization, recrystallization, phasic transfer and chromatography.

(4) Methods of synthesis of compound (I-D), wherein the group capable of releasing a cation is 2-thioxothiazolidin-4-one

Method F

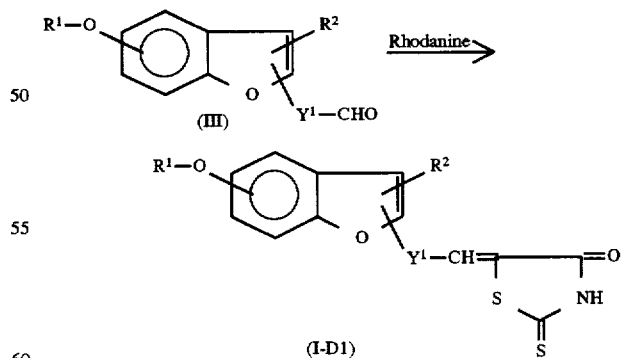

wherein the symbols have the same definitions as those given above.

In this method, a 2-thioxothiazolidin-4-one derivative (I-D1) is produced by condensation of aldehyde compound (III) with rhodanine. This reaction is carried out in the same manner as method B.

Compound (I-D1) thus obtained can be isolated and purified by known means of separation and purification such as ordinary concentration, concentration under reduced pressure, solvent extraction, crystallization, recrystallization, phasic transfer and chromatography, and may be obtained as a mixture of the (E)- and (Z)-configurations in terms of the double bond at the 5-position in the 2-thioxothiazolidin-4-one ring.

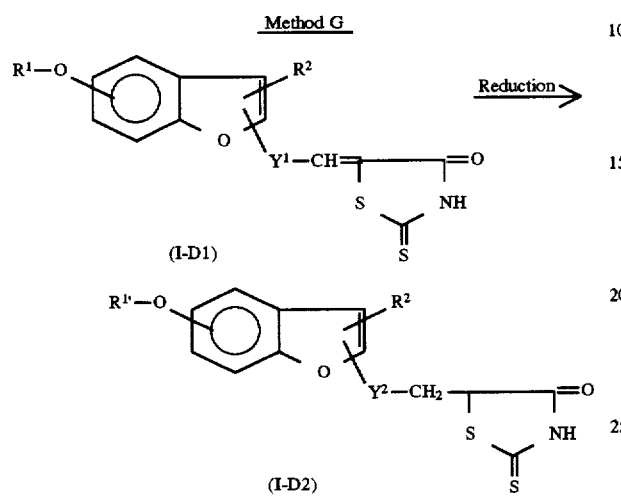

wherein the symbols have the same definitions as those given above.

In this method, compound (I-D2) is produced by reducing compound (I-D1) as obtained by method F. This reaction is carried out in the same manner as method C.

Compound (I-D2) thus obtained can be isolated and purified by known means of separation and purification such as ordinary concentration, concentration under reduced pressure, solvent extraction, crystallization, recrystallization, phasic transfer and chromatography.

(5) Methods of synthesis of compound (I-E), wherein the group capable of releasing a cation is 2,4-imidazolidinedione

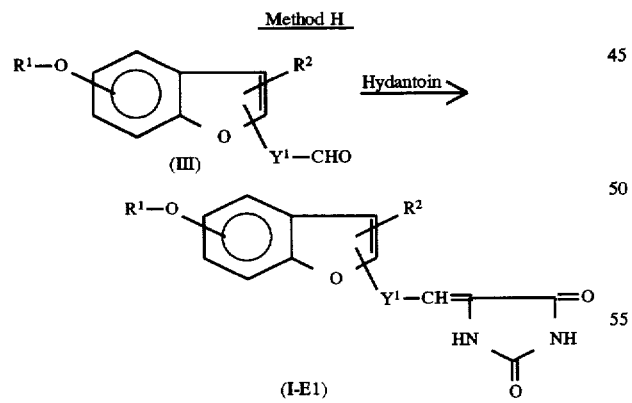

wherein the symbols have the same definitions as those given above.

In this method, 2,4-imidazolidinedione derivative (I-E1) is produced by condensation of aldehyde compound (III) with hydantoin. This reaction is carried out in the same manner as method B.

Compound (I-E1) thus obtained can be isolated and purified by known means of separation and purification such as ordinary concentration, concentration under reduced pressure, solvent extraction, crystallization, recrystallization, phasic transfer and chromatography. Compound (I-E1) may be obtained as a mixture of the (E)- and (Z)-configurations in terms of the double bond at the 5-position in the 2,4-imidazolidinedione ring.

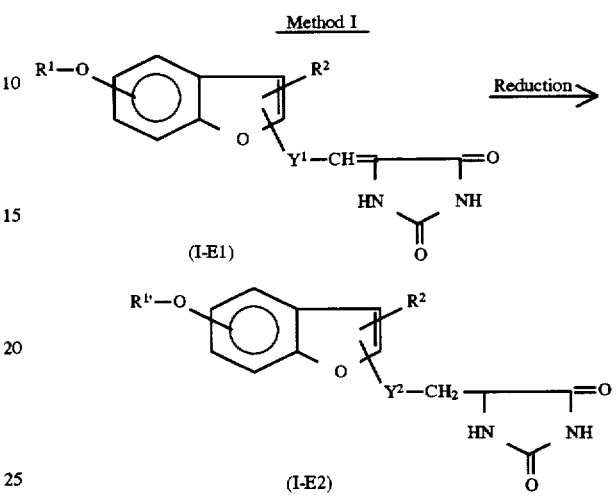

wherein the symbols have the same definitions as those given above.

In this method, compound (I-E2) is produced by reducing compound (I-E1) as obtained by method H. This reaction is carried out in the same manner as method C.

Compound (I-E2) thus obtained can be isolated and purified by known means of separation and purification such as ordinary concentration, concentration under reduced pressure, solvent extraction, crystallization, recrystallization, phasic transfer and chromatography.

(6) Methods of synthesis of compound (I-F), wherein the group capable of releasing a cation is 1,2,4-oxadiazol-5-one

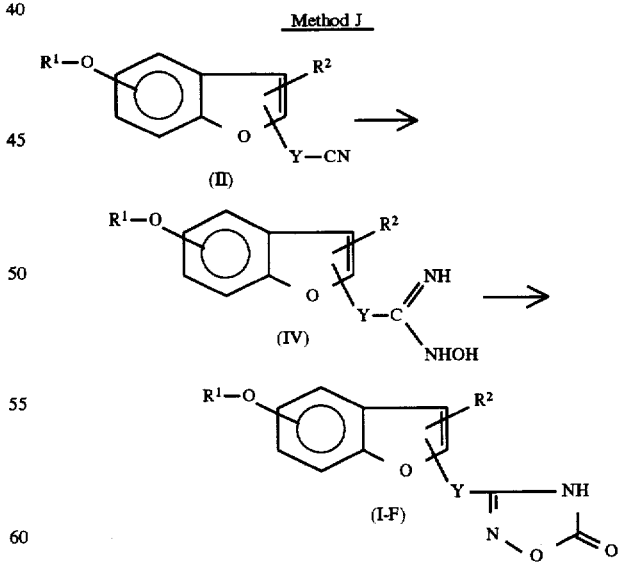

wherein the symbols have the same definitions as those given above.

In this method, oxadiazol-5-one compound (I-F) is produced by converting nitrile derivative (II) to amidoxime compound (IV), followed by cyclization.

The reaction for amidoxime compound (IV) from compound (II) is carried out in an ordinary organic solvent using about 2 to 10 mol of hydroxylamine per mol of compound (II). Such solvents include amides (e.g., N,N-dimethylformamide, N,N-dimethylacetamide), sulfoxides (e.g., dimethyl sulfoxide), alcohols (e.g., methanol, ethanol), ethers (e.g., dioxane, tetrahydrofuran) and halogenated hydrocarbons (e.g., dichloromethane, chloroform). When the hydroxylamine is used in the form of a salt with an inorganic acid (e.g., hydroxylamine hydrochloride, hydroxylamine sulfate) or a salt with an organic acid (e.g., hydroxylamine oxalate), the reaction is carried out in the presence of an appropriate base (e.g., potassium carbonate, sodium carbonate, sodium hydroxide, triethylamine, sodium methoxide, sodium ethoxide, sodium hydride) in an amount of about 1 mol equivalent, at 20° to 120° C. for about 1 to 24 hours.

Amidoxime compound (IV) thus obtained is reacted with a chlorocarbonic ester (e.g., methyl chlorocarbonate, ethyl chlorocarbonate) in the presence of a base (e.g., triethylamine, pyridine, potassium carbonate, sodium carbonate) in an ordinary solvent (e.g., chloroform, dichloromethane, dioxane, tetrahydrofuran, acetonitrile, pyridine) to yield an O-acyl compound. The reaction is normally carried out in the presence of 2 to 5 mol of the chlorocarbonic ester and 2 to 5 mol of the base, both per mol of amidoxime compound (IV). Reaction temperature is 0° to 50° C., reaction time being about 1 to 10 hours.

The reaction for cyclized compound (I-F) from the O-acylamidoxime compound thus obtained is carried out by heating in an ordinary solvent. Such solvents include aromatic hydrocarbons (e.g., benzene, toluene, xylene), ethers (e.g., dioxane, tetrahydrofuran) and halogenated hydrocarbons (e.g., dichloromethane, chloroform, dichloroethane). The reaction is carried out by treating the O-acylamidoxime compound in a solvent for 1 to 10 hours.

Compound (I-F) thus obtained can be isolated and purified by known means of separation and purification such as ordinary concentration, concentration under reduced pressure, solvent extraction, crystallization, recrystallization, phasic transfer and chromatography.

(7) Methods of synthesis of compound (I-G), wherein the group capable of releasing a cation is 1,2,4-oxadiazole-5-thione

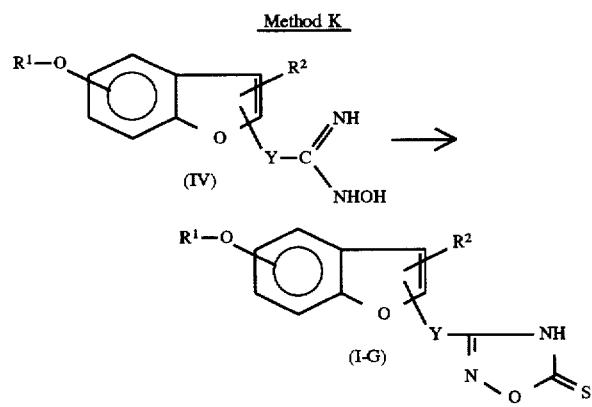

wherein the symbols have the same definitions as those given above.

In this method, thioketone compound (I-G) is produced by cyclizing amidoxime compound (IV) as obtained as a synthesis intermediate for compound (I-F) in method I above.

The reaction for thioketone compound (I-G) from amidoxime compound (IV) is carried out in an organic solvent, using about 1 to 10 mol of 1,1'-thiocarbonylimidazole per mol of amidoxime compound (IV). Such solvents include ethers (e.g., dioxane, tetrahydrofuran), halogenated hydrocarbons (e.g., dichloromethane, chloroform, dichloroethane), acetonitrile and acetone. Such bases include amines (e.g., pyridine, triethylamine, 2,6-dimethylpyridine, 1,5-diazabicyclo[4.3.0]non-5-ene and 1,8-diazabicyclo[5.4.0]-7-undecene). The reaction is preferably carried out in a solvent at −30° to 30° C. for about 0.5 to 10 hours.

Compound (I-G) thus obtained can be isolated and purified by known means of separation and purification such as ordinary concentration, concentration under reduced pressure, solvent extraction, crystallization, recrystallization, phasic transfer and chromatography.

(8) Methods of synthesis of compound (I-H), wherein the group capable of releasing a cation is 1,2,3,5-oxathiadiazole-2-oxide

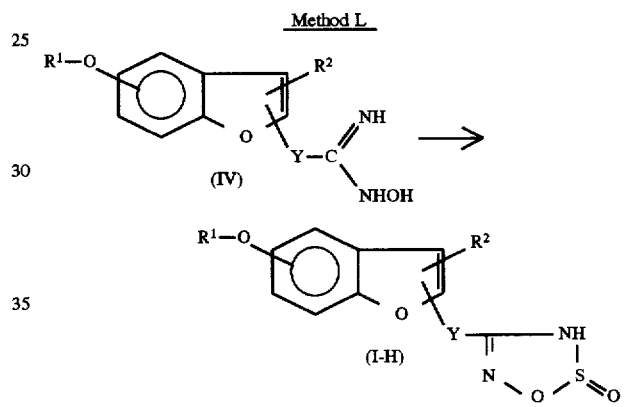

wherein the symbols have the same definitions as those given above.

In this method, 1,2,3,5-oxathiadiazole-2-oxide compound (I-H) is produced by cyclizing amidoxime compound (IV), which is obtained as a synthesis intermediate for compound (I-F) in method I above.

The reaction for 1,2,3,5-oxathiadiazole-2-oxide compound (I-H) from amidoxime compound (IV) is carried out by reacting amidoxime compound (IV) with thionyl chloride in an organic solvent (e.g., dioxane, tetrahydrofuran, dichloromethane, chloroform) in the presence of a base (e.g., pyridine, triethylamine) to yield compound (I-H).

This reaction is preferably carried out by adding about 2 to 10 mol of thionyl chloride in the presence of about 1 to 3 mol of base, both per mol of amidoxime compound (IV), in a solvent at −30° to 30° C. for about 0.5 to 10 hours.

Compound (I-H) thus obtained can be isolated and purified by known means of separation and purification such as ordinary concentration, concentration under reduced pressure, solvent extraction, crystallization, recrystallization, phasic transfer and chromatography.

(9) Methods of synthesis of compound (I-I), wherein the group capable of releasing a cation is 1,2,4-oxadiazolidine-3,5-dione

Method M

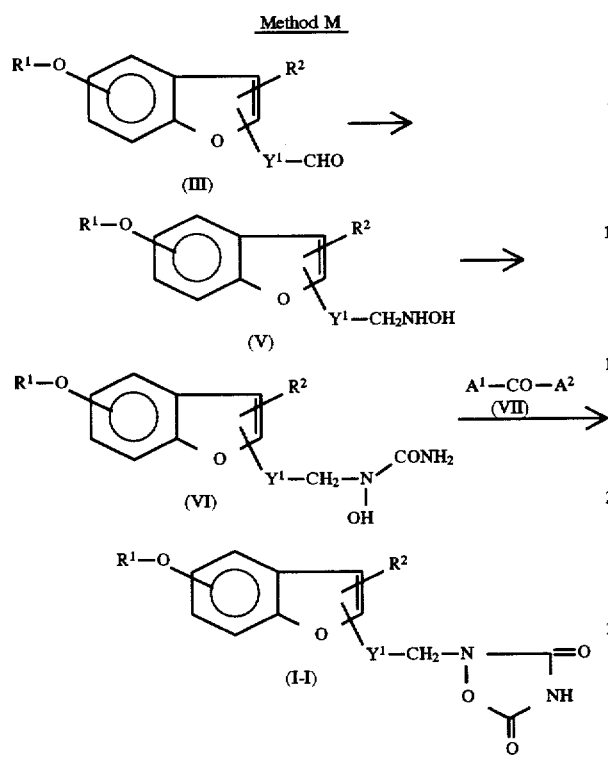

In formula (VII), A¹ and A², which can be the same or different, represent a halogen atom, an alkoxy group, an aralkyloxy group or an aryloxy group; the other symbols have the same definitions as those given above.

The halogen atom represented by A¹ or A² is exemplified by chlorine, bromine and iodine; the alkoxy group is exemplified by lower alkoxy groups (e.g., those having 1 to 4 carbon atoms, such as methoxy, ethoxy, propoxy and butoxy); the aralkyloxy group is exemplified by those having 7 to 13 carbon atoms, such as benzyloxy group; the aryloxy group is exemplified by those having 6 to 14 carbon atoms, such as phenoxy group.

In this method, compound (V) is produced by reacting aldehyde (III) with hydroxylamine or a salt thereof in a solvent inert to the reaction, specifically an organic solvent, e.g., an alcohol such as methanol or ethanol, or an aromatic hydrocarbon such as benzene, toluene or xylene, water or a mixture thereof, in the presence of a catalyst added if necessary, such as sodium acetate or p-toluene-sulfonic acid, using an azeotropic dehydrator or a dehydrating agent if necessary, and reducing the resulting Schiff base using a reducing agent commonly used for reductive amination, such as borane-pyridine complex or sodium borohydride. Compound (V) is then reacted with an alkali metal cyanate in an organic solvent inert to the reaction, e.g., an alcohol such as methanol or ethanol, or an ether such as tetrahydrofuran, or a mixture thereof, in the presence of an acidic catalyst added if necessary, such as hydrochloric acid, to yield compound (VI). By reacting compound (VI) with a carbonyl compound represented by the formula (VII), compound (I-I) can be produced. This reaction is preferably carried out in an organic solvent (e.g., dioxane, tetrahydrofuran, ether, dimethoxyethane, methanol, ethanol, 2-methoxyethanol, dimethyl sulfoxide) in a ratio of about 1 to 3 mol of compound (VII) per mol of compound (VI) in the presence of a base (e.g., sodium hydroxide, potassium hydroxide) at 0° to 150° C.

Compound (I-I) thus obtained can be isolated and purified by known means of separation and purification such as ordinary concentration, concentration under reduced pressure, solvent extraction, crystallization, recrystallization, phasic transfer and chromatography.

(10) Methods of synthesis of compound (II), wherein the group capable of releasing a cation is cyano group

Method N

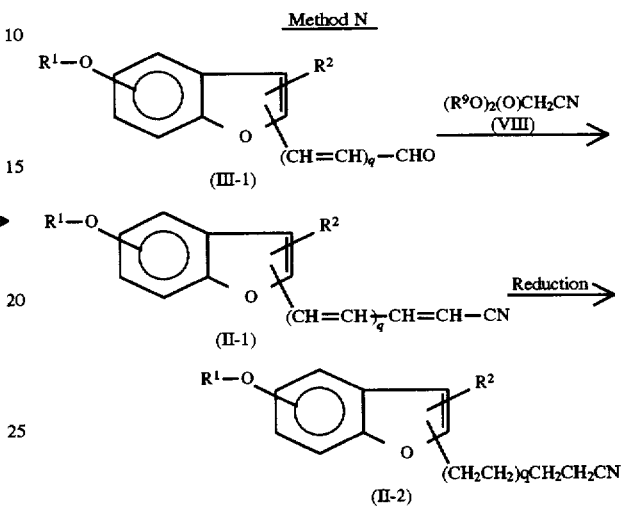

wherein $R^9$ represents a lower alkyl group; q represents 0, 1 or 2; the other symbols have the same definitions as those given above.

The lower alkyl group for $R^9$ is exemplified by alkyl groups having 1 to 4 carbon atoms, such as methyl, ethyl, propyl, isopropyl and butyl.

In this method, unsaturated nitrile derivative (II-1) is first produced by reacting aldehyde derivative (III-1) with cyanomethylphosphonate ester derivative (VIII). The reaction of compound (III-1) with compound (VIII) is carried out in an appropriate solvent in the presence of a base by a conventional method. The solvent is exemplified by aromatic hydrocarbons such as benzene, toluene and xylene; ethers such as dioxane, tetrahydrofuran and di-methoxyethane; alcohols such as methanol, ethanol and propanol; halogenated hydrocarbons such as chloroform, dichloromethane and 1,2-dichloroethane; N,N-dimethylformamide and dimethyl sulfoxide and mixtures thereof. The base is exemplified by alkali metal salts such as potassium hydroxide, sodium hydroxide, potassium carbonate, sodium carbonate and sodium hydrogen carbonate; amines such as pyridine, triethylamine and N,N-dimethylaniline; metal hydrides such as sodium hydride and potassium hydride; sodium ethoxide, sodium methoxide and potassium tert-butoxide. The amount of these bases used is preferably about 1 to 5 mol per mol of compound (III-1). The amount of compound (VIII) used is normally about 1 to 5 mol, preferably 1 to 3 mol, per mol of compound (III-1). This reaction is normally carried out at −50° to 150° C., preferably −10° to 100° C. Reaction time is 0.5 to 30 hours. Compound (II-1) is then subjected to catalytic reduction to yield compound (II-2). This reaction is carried out in the same manner as method C. Nitrile compounds (II-1) and (II-2) thus obtained can be isolated and purified by known means of separation and purification such as concentration, solvent extraction, crystallization, recrystallization, phasic transfer and chromatography.

Method O

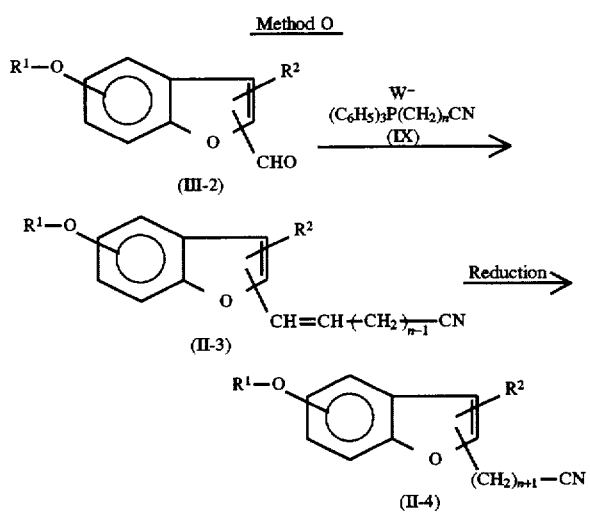

wherein n represents an integer from 1 to 6; W represents a halogen atom; the other symbols have the same definitions as those given above.

The halogen atom for W is exemplified by chlorine, bromine and iodine.

In this method, compound (II-3) is first produced by condensing aldehyde derivative (III-2) with phosphonium salt (IX). This reaction is carried out in an appropriate solvent, in the presence of a base, by a conventional method. The solvent, is exemplified by aromatic hydrocarbons such as benzene, toluene and xylene; ethers such as dioxane, tetrahydrofuran and dimethoxyethane; alcohols such as methanol, ethanol and propanol; halogenated hydrocarbons such as chloroform, dichloromethane and 1,2-dichloroethane; N,N-dimethylformamide, dimethyl sulfoxide and mixtures thereof. The base is exemplified by alkali metal salts such as potassium hydroxide, sodium hydroxide, potassium carbonate, sodium carbonate and sodium hydrogen carbonate; amines such as pyridine, triethylamine and N,N-dimethylaniline; metal hydrides such as sodium hydride and potassium hydride; sodium ethoxide, sodium methoxide and potassium tert-butoxide. The amount of these bases used is preferably about 1 to 5 mol per mol of compound (III-2). The amount of compound (IX) used is normally about 1 to 5 mol, preferably 1 to 3 mol, per mol of compound (III-2). This reaction is normally carried out at $-50°$ to $150°$ C., preferably $-10°$ to $100°$ C. Reaction time is 0.5 to 30 hours. Compound (II-3) is then subjected to catalytic reduction to yield compound (II-4). This reducing reaction is carried out in the same manner as method C. Nitrile compounds (II-3) and (II-4) thus obtained can be isolated and purified by known means of separation and purification such as concentration, solvent extraction, crystallization, recrystallization, phasic transfer and chromatography.

Method P

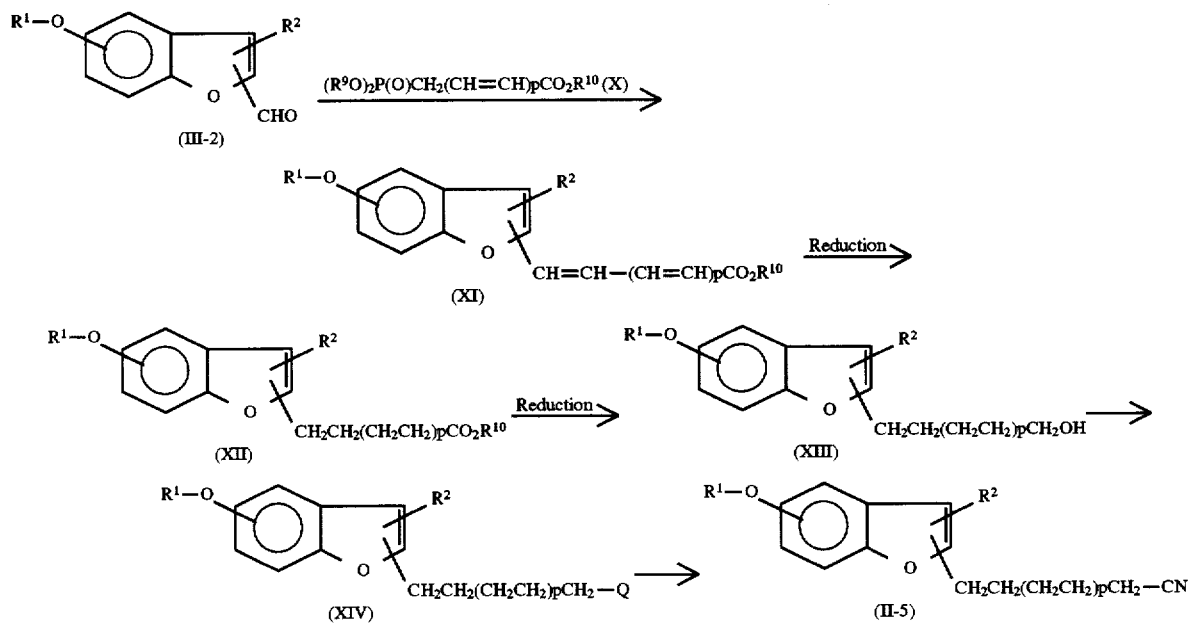

wherein $R^{10}$ represents a lower alkyl group; p represents 0, 1, or 2; Q represents a leaving group; the other symbols have the same definitions as those given above.

The lower alkyl group for $R^{10}$ is similar to that mentioned to exemplify the lower alkyl group for $R^9$. The leaving group for Q is exemplified by halogen atoms such as chlorine, bromine and iodine, and methanesulfonyloxy, benzenesulfonyloxy and p-toluenesulfonyloxy.

In this method, unsaturated ester derivative (XI) is first produced by condensing aldehyde derivative (III-2) with compound (X). This reaction is carried out in the same manner as the reaction of compound (III-1) with compound (VIII) in method N. Compound (XI) is then subjected to catalytic reduction to yield saturated ester derivative (XII). This reducing reaction is carried out in the same manner as method C.

Compound (XII) is then subjected to reduction to yield alcohol derivative (XIII). This reducing reaction can be carried out by a per se known method, such as reduction using a metal hydride, reduction using a metal-hydrogen complex compound, or reduction using diborane or substituted borane. Specifically, this reaction is carried out by treating compound (XII) with a reducing agent. Reducing agents include alkali metal borohydrides such as sodium borohydride and lithium borohydride, metal-hydrogen complex compounds such as lithium aluminum hydride, and borane compounds. This reaction is carried out in a solvent that does not interfere with the reaction. The solvent is exemplified by aromatic hydrocarbons such as benzene, toluene and xylene; ethers such as dioxane, tetrahydrofuran and dimethoxyethane; alcohols such as methanol, ethanol and propanol; halogenated hydrocarbons such as chloroform, dichloromethane and 1,2-dichloroethane; N,N-dimethylformamide and dimethyl sulfoxide and mixtures thereof, selected depending on the kind of reducing agent used. Reaction temperature is normally −50° to 150° C., preferably −10° to 100° C. Reaction time is 0.5 to 30 hours.

Compound (XIII) is then reacted with a halogenating agent or sulfonylating agent to yield compound (XIV). Preferable halogenating agents include hydrochloric acid, thionyl chloride and phosphorus tribromide. When a halogenating agent is used, compound (XIV) having chlorine or bromine for Q is produced. This reaction is carried out in an appropriate inert solvent (e.g., benzene, toluene, xylene, chloroform, dichloromethane) or an excess halogenating agent as a solvent at −10° to 80° C. The amount of halogenating agent used is 1 to 20 mol per mol of compound (XIII). Preferable sulfonylating agents include methanesulfonyl chloride, p-toluenesulfonyl chloride and benzenesulfonyl chloride. When these sulfonylating agents are used, compound (XIV) respectively having methanesulfonyloxy, p-toluenesulfonyloxy or benzenesulfonyloxy for Q is produced. This reaction is carried out in an appropriate inert solvent (e.g., benzene, toluene, xylene, diethyl ether, ethyl acetate, tetrahydrofuran, chloroform, dichloromethane) in the presence of a base (e.g., triethylamine, N-methylmorpholine, sodium hydrogen carbonate, potassium hydrogen carbonate, sodium carbonate, potassium carbonate) at −10° to 30° C. The amounts of sulfonylating agent and base used are each 1 to 2 mol per mol of compound (XIII). Compound (XIV) having chlorine, bromine or sulfonyloxy for Q thus obtained can be reacted with 1 to 2 mol of sodium iodide or potassium iodide per mol of compound (XIV) to yield compound (XIV) having iodine for Q. This reaction is carried out in a solvent such as acetone, 2-butanone, methanol or ethanol at 20° to 80° C.

Compound (XIV) is then reacted with potassium cyanide or sodium cyanide to yield compound (II-5). This reaction is normally carried out in a solvent (e.g., diethyl ether, tetrahydrofuran, dioxane, ethyl acetate, methanol, ethanol, chloroform, dichloromethane, acetone, 2-butanone, N,N-dimethylformamide, dimethyl sulfoxide) at 0° to 100° C. The amount of potassium cyanide or sodium cyanide used is 1 to 5 mol per mol of compound (XIV). Nitrile compound (II-5) thus obtained can be isolated and purified by known means of separation and purification such as concentration, solvent extraction, crystallization, recrystallization, phasic transfer and chromatography.

Compound (II) described above can be used as a starting material in the above Method A or Method J.

(11) Methods of synthesis of compounds (XI) and (XII), wherein the group capable of releasing a cation is alkoxycarbonyl group.

Compounds (XI) and (XII) can be produced according to Method P described above.

Compounds (XI) and (XII) thus obtained can be isolated and purified by known means of separation and purification such as concentration, solvent extraction, crystallization, recrystallization, phasic transfer and chromatography.

(12) Methods of synthesis of compounds, wherein the group capable of releasing a cation is carboxyl group.

Compound (II), (XI) or (XII) is subjected to hydrolysis to produce a compound wherein the group capable of releasing a cation is carboxyl group.

Hydrolysis is carried out by the contact of a base or an acid, in a solvent which does not interfere with the reaction. The solvent is exemplified by alcohols such as methanol, ethanol, propanol; ethers such as dioxane, tetrahydrofuran, dimethoxyethane; N,N-dimethylformamide and mixtures thereof. The base is exemplified by alkali metal salts such as potassium hydroxide, sodium hydroxide, potassium carbonate, sodium carbonate and sodium hydrogen carbonate. The amount of these bases used is 1 to 3 mol per mol of a starting material. The acid is exemplified by hydrochloric acid, hydrobromic acid and p-toluenesulfonic acid. The amount of these acids used is normally 1 mol to excess per mol of a starting material. When an acid is used, an excess amount of the acid can be used as a solvent. The reaction temperature is −50° to 150° C., preferably −10° to 100° C. The reaction time is 0.5 to 30 hours.

Compounds thus obtained can be isolated and purified by known means of separation and purification such as concentration, solvent extraction, crystallization, recrystallization, phasic transfer and chromatography.

Aldehyde derivative (III) as a starting material for methods B, D, F, H, M, N, O and P described above can, for example, be produced by methods Q and R as follows:

Method Q

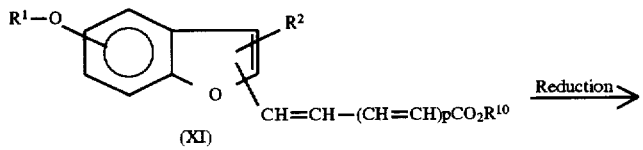

Method Q

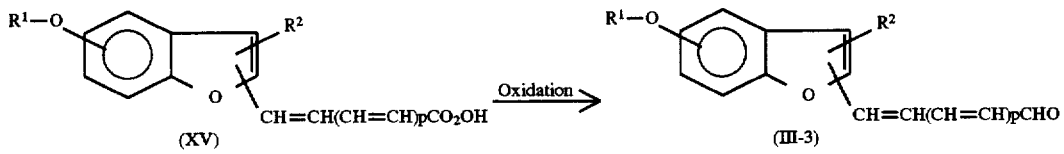

wherein the symbols have the same definitions as those given above.

In this method, unsaturated ester derivative (XI) is first subjected to reducing reaction to yield alcohol derivative (XV). Although this reducing reaction is carried out in the same manner as the reducing reaction of compound (XII) in method P, it is advantageous to use diisobutylaluminum hydride as a reducing agent. Compound (XV) is then subjected to oxidizing reaction to yield unsaturated aldehyde derivative (III-3). This oxidizing reaction can be carried out by a per se known method, such as oxidation using manganese dioxide, oxidation using chromic acid or oxidation using dimethyl sulfoxide. Specifically, this reaction is carried out by treating compound (XV) with an oxidizing agent. Although useful oxidizing agents include manganese dioxide and chromic anhydride, it is advantageous to use manganese dioxide. This reaction is carried out in a solvent that does not interfere with the reaction. The solvent is exemplified by aromatic hydrocarbons such as benzene, toluene and xylene; ethers such as dioxane, tetrahydrofuran and dimethoxyethane; halogenated hydrocarbons such as chloroform, dichloromethane and 1,2-dichloroethane; N,N-dimethylformamide, dimethyl sulfoxide and mixtures thereof, selected depending on the kind of oxidizing agent used. Reaction temperature is normally –50° to 150° C., preferably –10° to 100° C. Reaction time is 0.5 to 30 hours.

Aldehyde derivative (III-3) thus obtained can be isolated and purified by known means of separation and purification such as concentration, solvent extraction, crystallization, recrystallization, phasic transfer and chromatography.

Method R

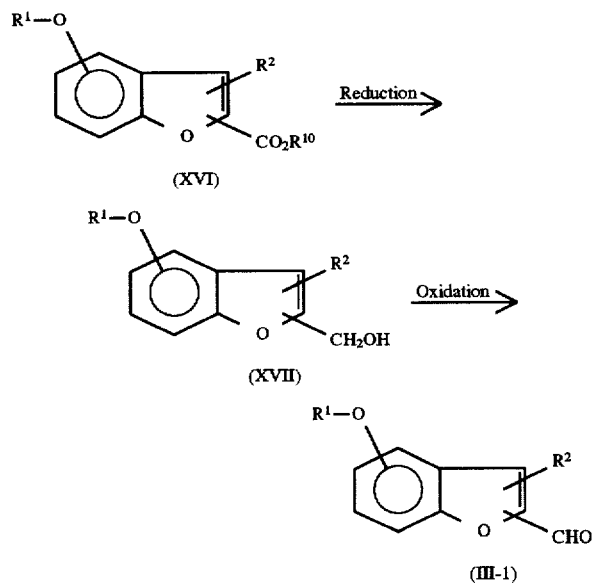

wherein the symbols have the same definitions as those given above.

This method is carried out in the same manner as method Q. Specifically, compound (III-1) can be obtained by reducing compound (XVI) in the same manner as the reducing reaction of compound (XI) in method Q, and oxidizing compound (XVII) in the same manner as the oxidizing reaction of compound (XV) in method Q.

Aldehyde derivative (III-1) thus obtained can be isolated and purified by known means of separation and purification such as concentration, solvent extraction, crystallization, recrystallization, phasic transfer and chromatography.

Starting material compound (XVI) for method R can, for example, be produced by the method described below.

Method S

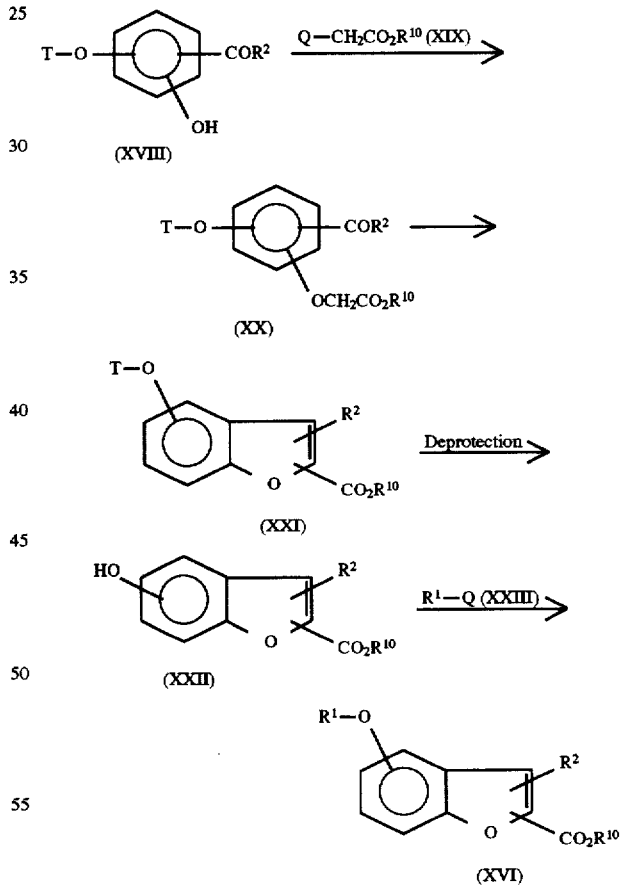

wherein T represents a lower alkyl group, an aralkyl group or an acyl group; the other symbols have the same definitions as those given above.

The lower alkyl group for T is exemplified by those having 1 to 4 carbon atoms, such as methyl, ethyl, propyl, isopropyl, butyl and tert-butyl; the aralkyl group is exemplified by those having 7 to 19 carbon atoms, such as benzyl, diphenylmethyl and trityl; the acyl group is exemplified by lower alkyl groups having 1 to 4 carbon atoms or aromatic hydrocarbons having 6 to 14 carbon atoms all having a carbonyl group bound thereto, such as acetyl, propionyl and benzoyl.

In this method, compound (XVIII), which has a hydroxyl group having protecting group T as a substituent, and compound (XIX), are condensed to yield compound (XX). This reaction is carried out in the presence of a base in an appropriate solvent by a conventional method. The solvent is exemplified by aromatic hydrocarbons such as benzene, toluene and xylene; ethers such as dioxane, tetrahydrofuran and dimethoxyethane; alcohols such as methanol, ethanol and propanol; halogenated hydrocarbons such as chloroform, dichloromethane and 1,2-dichloroethane; N,N-dimethylformamide, dimethyl sulfoxide and mixtures thereof. The base is exemplified by alkali metal salts such as sodium hydroxide, potassium hydroxide, potassium carbonate, sodium carbonate and sodium hydrogen carbonate; amines such as pyridine, triethylamine and N,N-dimethylaniline; metal hydrides such as sodium hydride and potassium hydride; sodium ethoxide, sodium methoxide and potassium tert-butoxide. The amount of these bases used is preferably about 1 to 5 mol per mol of compound (XVIII). The amount of compound (XIX) used is normally about 1 to 5 mol, preferably 1 to 3 mol, per mol of compound (XVIII). This reaction is normally carried out at −20° to 180° C., preferably 0° to 120° C. Reaction time is 0.5 to 30 hours.

Compound (XX) is then subjected to intramolecular condensation to yield compound (XXI). This reaction is carried out in the presence of a base in an appropriate solvent by a conventional method. The solvent is exemplified by aromatic hydrocarbons such as benzene, toluene and xylene; ethers such as dioxane, tetrahydrofuran and dimethoxyethane; alcohols such as methanol, ethanol and propanol; halogenated hydrocarbons such as chloroform, dichloromethane and 1,2-dichloroethane; ethyl acetate, pyridine, acetonitrile, N,N-dimethylformamide, dimethyl sulfoxide, acetic acid, acetic anhydride and mixtures thereof. The base is exemplified by alkali metal salts such as potassium hydroxide, sodium hydroxide, potassium carbonate, sodium carbonate, sodium hydrogen carbonate, sodium acetate and potassium acetate; amines such as pyridine, triethylamine, N,N-dimethylaniline and 1,8-diazabicyclo[5.4.0]-7-undecene; metal hydrides such as sodium hydride and potassium hydride; sodium ethoxide, sodium methoxide and potassium tert-butoxide. The amount of these bases used is preferably about 1 to 5 mol per mol of compound (XX). This reaction is normally carried out at −20° to 180° C., preferably 0° to 120° C. Reaction time is 0.5 to 30 hours.

Compound (XXI) is then deprotected to yield compound (XXII). This reaction is carried out by a conventional method chosen as appropriate depending on the kind of protecting group T used. Compound (XXII) and compound (XXIII) are then condensed to yield compound (XVI). This reaction is carried out in the same manner as the reaction of compound (XXIII) with compound (XIX). Compound (XVI) thus obtained can be isolated and purified by known means of separation and purification such as concentration, solvent extraction, crystallization, recrystallization, phasic transfer and chromatography.

The following experimental example, examples, formulation examples and reference examples are merely intended to illustrate the present invention in further detail but should by no means be construed as defining the scope of the invention.

EXPERIMENTAL EXAMPLE

Hypoglycemic and hypolipidemic activity in mice

KKA$^y$ mice (9 to 14 week old) were fed with powdery feed (CE-2, Clea Japan Inc.) containing the subject compound at a rate of 0.005% for 4 days, during which the animals were allowed to access freely to water. Blood was collected via the orbital cavity venous plexus. Using the plasma, glucose and triglyceride were determined quantitatively by the enzyme method using the Iatrochem-GLU (A) kit (IATRON LABORATORIES, INC.) and Iatro-MA701 TG kit (IATRON LABORATORIES, INC.), respectively. The respective values in drug-dosed groups are shown in terms of percent reduction (%) compared to non-drug-dosed groups, which are shown in Table 1.

TABLE 1

| Compound (Example number) | Hypoglycemic Action (%) | Hypolipidemic Action (%) |
|---|---|---|
| 2 | 61 | 92 |
| 6 | 40 | 27 |
| 7 | 38 | 26 |
| 8 | 61 | 70 |

As is evident from these results, the compound (I) of the present invention possesses excellent hypoglycemic and hypolipidemic activity, and is pharmaceutically useful as a therapeutic agent for diabetes mellitus, an agent for enhancing insulin sensitivity, a therapeutic agent for hyperlipidemia and a therapeutic agent for hypertension.

Example 1

A mixture of 2-(2-cyanoethyl)-6-(5-methyl-2-phenyl-4-oxazolylmethoxy)benzofuran (1.20 g), sodium azide (1.09 g), ammonium chloride (0.90 g) and N,N-dimethylformamide (30 ml) was stirred at 130° to 140° C. for 16 hours. The reaction mixture was poured over water and extracted with ethyl acetate. After the ethyl acetate layer was washed with water and dried (MgSO$_4$), the solvent was distilled off; the residue was subjected to silica gel column chromatography. From the fraction eluted with methanol-chloroform (5:95, v/v), 5-[2-|6-(5-methyl-2-phenyl-4-oxazolylmethoxy)-2-benzofuranyl]ethyl ]-1H-tetrazole (1.05 g, 78%) was obtained, which was then recrystallized from dichloromethane-methanol to yield colorless prisms having a melting point of 177° to 178° C.

Elemental analysis for $C_{22}H_{19}N_5O_3$: Calculated: C, 65.83; H, 4.77; N, 17.45 Found: C, 65.57; H, 4.97, N, 17.44

Example 2

5-[3-|6-(5-Methyl-2-phenyl-4-oxazolylmethoxy)-2-benzofuranyl]propyl]-1H-tetrazole was obtained in the same manner as in Example 1 (yield 58%), which was then recrystallized from dichloromethane-methanol to yield colorless prisms having a melting point of 139° to 140° C.

Example 3

5-[4-[6-(5-Methyl-2-phenyl-4-oxazolylmethoxy)-2-benzofuranyl]butyl|-1H-tetrazole was obtained in the same manner as in Example 1 (yield 55%), which was then recrystallized from dichloromethane-isopropyl ether to yield colorless prisms having a melting point of 114° to 115° C.

Example 4

A mixture of 6-(5-methyl-2-phenyl-4-oxazolylmethoxy) benzofuran-2-carbaldehyde (1.20 g), 2,4-thiazolidinedione (0.465 g), piperidine (0.12 g) and ethanol (40 ml) was heated under refluxing conditions for 2 hours. After the mixture was cooled, the resulting crystals of 5-[6-(5-methyl-2-phenyl-4-oxazolylmethoxy)-2-benzofuranyl-methylidene]-2,4-thiazolidinedione (1.46 g, 94%) were collected, which was then recrystallized from chloroformethanol to yield yellow prisms having a melting point of 272° to 273° C.

Elemental analysis for $C_{23}H_{16}N_2O_5S \cdot \frac{1}{4}H_2O$: Calculated: C, 63.22; H, 3.81; N, 6.41 Found: C, 63.16; H, 3.62, N, 6.31

Example 5

A mixture of 5-[6-(5-methyl-2-phenyl-4-oxazolylmethoxy)-2-benzofuranylmethylidene]-2,4-thiazolidinedione (0.80 g), palladium-carbon (5%, 1.60 g) and tetrahydrofuran (250 ml) was subjected to catalytic reduction at room temperature under a hydrogen pressure of 3.2 kgf/cm² for 8 hours. After the catalyst was filtered off, the filtrate was subjected to catalytic reduction under constant conditions for additional 16 hours. After the catalyst was filtered off, the filtrate was concentrated under reduced pressure; the residue was subjected to silica gel column chromatography. From the fraction eluted with ethyl acetate-chloroform (1:5, v/v), crystals of 5-[6-(5-methyl-2-phenyl-4-oxazolylmethoxy)-2-benzofuranylmethyl]-2,4-thiazolidinedione (0.305 g, 38%) were obtained, which was then recrystallized from dichloromethane-methanol to yield yellow needles having a melting point of 179° to 180° C.

Elemental analysis for $C_{23}H_{18}N_2O_5S$: Calculated: C, 63.58; H, 4.18; N, 6.45 Found: C, 63.51; H, 3.96, N, 6.52

Example 6

A mixture of (E)-3-[6-(5-methyl-2-phenyl-4-oxazolylmethoxy)-2-benzofuranyl]acrolein (1.00 g), 2,4-thiazolidinedione (0.49 g), piperidine (0.24 g) and acetic acid (20 ml) was heated under refluxing conditions for 2 hours. The reaction mixture was concentrated under reduced pressure; the resulting crystals (0.79 g) were collected by filtration. The crystals were dissolved in tetrahydrofuran (200 ml); after palladium-carbon (5%, 1.60 g) was added, the mixture was subjected to catalytic reduction under a hydrogen pressure of 3.2 kgf/cm² for 8 hours. After the catalyst was filtered off, the filtrate was subjected to catalytic reduction under constant conditions for additional 8 hours. After the catalyst was filtered off, the filtrate was concentrated under reduced pressure; the residue was subjected to silica gel column chromatography. From the fraction eluted with ethyl acetate-chloroform (1:9, v/v), crystals of 5-[3-[6-(5-methyl-2-phenyl-4-oxazolylmethoxy)-2-benzofuranyl]propyl]-2,4-thiazolidinedione (0.34 g, 26%) were obtained, which was then recrystallized from dichloromethane-methanol to yield yellow prisms having a melting point of 167° to 168° C.

Elemental analysis for $C_{25}H_{22}N_2O_5S$: Calculated: C, 64.92; H, 4.79; N, 6.06 Found: C, 64.63; H, 4.85, N, 5.95

Example 7

A mixture of 6-(5-methyl-2-phenyl-4-oxazolylmethoxy)-2-benzofurancarbaldehyde (1.70 g), 2,4-oxazolidinedione (1.55 g), pyrrolidine (0.365 g) and ethanol (40 ml) was heated under refluxing conditions for 3 hours. The reaction mixture was poured over water; the resulting crystals were collected by filtration. The crystals were dissolved in tetrahydrofuran (100 ml); after palladium-carbon (0.40 g) was added, the mixture was subjected to catalytic reduction at room temperature under an atmospheric pressure of 1 atm. After the catalyst was filtered off, the filtrate was concentrated under reduced pressure; the residue was subjected to silica gel column chromatography. From the fraction eluted with methanolchloroform (2:98, v/v), crystals of 5-[6-(5-methyl-2-phenyl-4-oxazolylmethoxy)-2-benzofuranylmethyl]-2,4-oxazolidinedione (0.14 g, 6.6%) were obtained, which was then recrystallized from dichloromethane-methanol to yield colorless prisms having a melting point of 172° to 173° C.

Elemental analysis for $C_{23}H_{18}N_2O_6$: Calculated: C, 66.03; H, 4.34; N, 6.70 Found: C, 65.95; H, 4.31, N, 6.71

Example 8

5-[3-[6-(5-Methyl-2-phenyl-4-oxazolylmethoxy)-2-benzofuranyl]propyl]-2,4-oxazolidinedione was obtained in the same manner as in Example 7 (yield 25%), which was then recrystallized from dichloromethane-methanol to yield light-yellow prisms having a melting point of 159° to 160° C.

Example 9

5-[3-[5-(5-Methyl-2-phenyl-4-oxazolylmethoxy)-2-benzofuranyl]propyl]-1H-tetrazole was obtained in the same manner as in Example 1 (yield 82%), which was then recrystallized from acetone-isopropylether to yield colorless prisms having a melting point of 136° to 137° C.

Example 10

Sodium hydride (60%, oily, 0.20 g) was gradually added to a solution of 6-(5-methyl-2-phenyl-4-oxazolylmethoxy)benzofuran-2-carbaldehyde (1.50 g) and diethyl cyanomethylphosphonate (0.88 g) in N,N-dimethylformamide (30 ml) at 0° C., followed by stirring at room temperature for 1 hour. The reaction mixture was poured over ice water and neutralized with 2N hydrochloric acid, followed by extraction with ethyl acetate (200 ml). After the ethyl acetate layer was washed with water and dried (MgSO₄), palladium-carbon (5%, 0.70 g) was added, followed by catalytic reduction at room temperature under an atmospheric pressure of 1 atm. After the catalyst was filtered off, the filtrate was concentrated; the residue was subjected to silica gel column chromatography. From the fraction eluted with ethyl acetate-chloroform (2:98, v/v), crystals of 2-(2-cyanoethyl)-6-(5-methyl-2-phenyl-4-oxazolylmethoxy)benzofuran (1.34 g, 83%) were obtained, which was then recrystallized from dichloromethane-hexane to yield colorless prisms having a melting point of 92° to 93° C.

Example 11

Sodium hydride (60%, oily, 0.20 g) was gradually added to a solution of 3-cyanopropyltriphenylphosphonium bromide (2.07 g) in N,N-dimethylformamide (30 ml) at room temperature, followed by stirring for 1 hour. 6-(5-Methyl-2-phenyl-4-oxazolylmethoxy)benzofuran-2-carboaldehyde (1.40 g) was added, followed by stirring at 70° to 80° C. for 2 hours. The reaction mixture was poured over ice water and neutralized with 2N hydrochloric acid, followed by extraction with ethyl acetate (200 ml). After the ethyl acetate layer was washed with water and dried (MgSO₄), the solvent was distilled off; the residue was subjected to silica gel column chromatography. From the fraction eluted with ethyl acetate-hexane (1:2, v/v), an oily substance was obtained, which was dissolved in tetrahydrofuran (40 ml). To this solution, palladium-carbon (5%, 0.70 g) was added, followed by catalytic reduction at room temperature and under an atmospheric pressure of 1 atm. The catalyst was filtered off, the filtrate was concentrated; the residue was subjected to silica gel column chromatography. From the fraction eluted with ethyl acetate-hexane (1:3, v/v), crystals of 2-(4-cyanobutyl)-6-(5-methyl-2-phenyl-4-oxazolylmethoxy)benzofuran (0.97 g, 60%) were obtained, which was then recrystallized from diethyl ether-hexane to yield colorless prisms having a melting point of 87° to 88° C.

Example 12

Sodium hydride (60%, oily, 0.72 g) was gradually added to a solution of 6-(5-methyl-2-phenyl-4-oxazolylmethoxy)benzofuran-2-carbaldehyde (6.00 g) and triethyl phosphonoacetate (4.04 g) in N,N-dimethylformamide (100 ml) at 0° C., followed by stirring for 1 hour. The reaction mixture was poured over ice water; the resulting crystals of (E)-ethyl 3-[6-(5-methyl-2-phenyl-4-oxazolylmethoxy)-2-benzofuranyl]acrylate were obtained, which was then recrystallized from dichloromethane-ethanol to yield colorless prisms (7.03 g, 97%) having a melting point of 141° to 142° C.

Example 13

A mixture of 3-[6-(5-methyl-2-phenyl-4-oxazolylmethoxy)-2-benzofuranyl]propanol (0.88 g), methanesulfonyl chloride (0.335 g), triethylamine (0.295 g) and dichloromethane (30 ml) was stirred at room temperature for 14 hours. After the reaction mixture was washed with 2N hydrochloric acid and dried ($MgSO_4$), the solvent was distilled off. The residue was dissolved in N,N-dimethylformamide (30 ml); to this solution, potassium cyanide (0.24 g) was added, followed by stirring at 90° to 100° C. for 4 hours. The reaction mixture was poured over water and neutralized with 2N hydrochloric acid, followed by extraction with ethyl acetate. After the ethyl acetate layer was washed with water and dried ($MgSO_4$), the solvent was distilled off; the residue was subjected to silica gel column chromatography. From the fraction eluted with ethyl acetate-hexane (1:4, v/v), crystals of 2-(3-cyanopropyl)-6-(5-methyl-2-phenyl-4-oxazolylmethoxy)benzofuran were obtained, which was then recrystallized from ethyl acetate-hexane to yield colorless prisms (0.65 g, 72%) having a melting point of 94° to 95° C.

Example 14

In the same manner as in Example 12, 5-(5-methyl-2-phenyl-4-oxazolylmethoxy)benzofuran-2-carbaldehyde was reacted with triethyl phosphonoacetate to yield (E)-ethyl 3-[5-(5-methyl-2-phenyl-4-oxazolylmethoxy)-2-benzofuranyl]acrylate (yield 93%), which was then recrystallized from acetone-isopropyl ether to yield colorless needles having a melting point of 120° to 121° C.

Example 15

In the same manner as in Example 13, 3-[5-(5-methyl-2-phenyl-4-oxazolylmethoxy)-2-benzofuranyl]propanol was mesylated and then reacted with sodium cyanide to yield 2-(3-cyanopropyl)-5-(5-methyl-2-phenyl-4-oxazolylmethoxy)benzofuran (yield 80%), which was then recrystallized from acetone-isopropyl ether to yield colorless prisms having a melting point of 114° to 115° C.

Formulation Example 1

| Formulation Example of Tablets | |
|---|---|
| (1) 5-[3-[6-(5-Methyl-2-phenyl-4-oxazolylmethoxy)-2-benzofuranyl]propyl]-1H-tetrazole (compound of Example 2) | 10 g |
| (2) Lactose | 50 g |
| (3) Corn starch | 15 g |
| (4) Carboxymethylcellulose calcium | 44 g |
| (5) Magnesium stearate | 1 g |
| 1,000 tablets | 120 g |

All portions of (1), (2) and (3), and 30 g of (4) were kneaded with water, which was subjected to vacuum drying, followed by granulation. Thus-granulated powder was mixed with, 14 g of (4) and 1 g of (5), followed by tableting using a tableting machine, to prepare 1,000 tablets each containing 10 mg of (1).

Formulation Example 2

| Formulation Example of Tablets | |
|---|---|
| (1) 5-[3-[6-(5-Methyl-2-phenyl-4-oxazolylmethoxy)-2-benzofuranyl]propyl]-2,4-oxazolidinedione (compound of Example 8) | 30 g |
| (2) Lactose | 50 g |
| (3) Corn starch | 15 g |
| (4) Carboxymethylcellulose calcium | 44 g |
| (5) Magnesium stearate | 1 g |
| 1,000 tablets | 140 g |

All portions of (1), (2) and (3), and 30 g of (4) were kneaded with water, which was subjected to vacuum drying, followed by granulation. Thus-granulated powder was mixed with, 14 g of (4) and 1 g of (5), followed by tableting using a tableting machine, to prepare 1,000 tablets each containing 30 mg of (1).

Reference Example 1

A mixture of 4-methoxysalicylaldehyde (21.0 g), methyl bromoacetate (22.2 g), potassium carbonate (22.9 g) and N,N-dimethylformamide (150 ml) was stirred at 90° to 100° C. for 1 hour. The reaction mixture was poured over ice water; the resulting crystals of methyl 2-formyl-5-methoxyphenoxyacetate (27.7 g, 90%) were collected by filtration and recrystallized from acetone-isopropyl ether to yield colorless prisms having a melting point of 109° to 110° C.

Reference Example 2

A mixture of methyl 2-formyl-5-methoxyphenoxyacetate (27.7 g), 1,8-diazabicyclo[5.4.0]-7-undecene (40.8 g) and toluene (200 ml) was heated under refluxing conditions for 4 hours. The reaction mixture was concentrated under reduced pressure; after 6N hydrochloric acid was added, the residue was extracted with ethyl acetate. After the ethyl acetate layer was washed with water and dried ($MgSO_4$), the solvent was distilled off; 10% hydrochloric acid-methanol (30 ml) was added to the residue, followed by heating at 70° to 80° C. for 4 hours. The reaction mixture was concentrated under reduced pressure; water was added, followed by extraction with ethyl acetate. After the ethyl acetate layer was washed with water and dried ($MgSO_4$), the solvent was distilled off; the residue was subjected to silica gel column chromatography. From the fraction eluted with chloroform-hexane (1:2, v/v), methyl 6-methoxybenzofuran-2-carboxylate (14.3 g, 57%) was obtained, which was then recrystallized from dichloromethane-isopropyl ether to yield colorless prisms having a melting point of 97° to 98° C.

Reference Example 3

Boron tribromide (24.9 g) was added dropwise to a solution of methyl 6-methoxybenzofuran-2-carboxylate (18.6 g) in dichloromethane (200 ml) at 0° C., followed by stirring at room temperature for 1 day. The reaction mixture was poured over ice water; ethyl acetate (300 ml) was added. After the organic layer was washed with water and dried (MgSO$_4$), the solvent was distilled off; 10% hydrochloric acid-methanol (60 ml) was added to the residue, followed by heating at 70° to 80° C. for 5 hours. The reaction mixture was concentrated under reduced pressure; the resulting crystals of methyl 6-hydroxybenzofuran-2-carboxylate (10.75 g) were collected by filtration using diethyl ether-isopropyl ether (2:1, v/v). The filtrate was concentrated; the residue was subjected to silica gel column chromatography. From the fraction eluted with diethyl ether-hexane (1:2, v/v), methyl 6-hydroxybenzofuran-2-carboxylate (1.75 g) was obtained (total yield 73%), which was then recrystallized from diethyl ether-isopropyl ether to yield colorless prisms having a melting point of 176° to 177° C.

Reference Example 4

A mixture of methyl 6-hydroxybenzofuran-2-carboxylate (1.75 g), 4-chloromethyl-5-methyl-2-phenyloxazole (2.00 g), potassium carbonate (1.51 g) and N,N-dimethylformamide (40 ml) was stirred at 80° to 90° C. for 1 hour. The reaction mixture was poured over ice water and neutralized with 2N hydrochloric acid, followed by extraction with ethyl acetate. The ethyl acetate layer was washed with water and dried (MgSO$_4$), the solvent was distilled off; the residue was subjected to silica gel column chromatography. From the fraction eluted with ethyl acetate-chloroform (1:99, v/v), crystals of methyl 6-(5-methyl-2-phenyl-4-oxazolylmethoxy)benzofuran-2-carboxylate (3.00 g, 91%) were obtained, which was then recrystallized from dichloromethane-isopropyl ether to yield colorless prisms having a melting point of 125° to 126° C.

Reference Example 5

Lithium aluminum hydride (0.285 g) was gradually added to a solution of methyl 6-(5-methyl-2-phenyl-4-oxazolylmethoxy)benzofuran-2-carboxylate (2.70 g) in tetrahydrofuran (40 ml) at 0° C., followed by stirring for 1 hour. After 1N hydrochloric acid was carefully added to the reaction mixture, water (300 ml) was added; the resulting crystals of 6-(5-methyl-2-phenyl-4-oxazolylmethoxy)benzofuran-2-methanol were collected by filtration, which was then recrystallized from chloroform-methanol to yield colorless prisms (2.17 g, 87%) having a melting point of 202° to 203° C.

Reference Example 6

A mixture of 6-(5-methyl-2-phenyl-4-oxazolylmethoxy)benzofuran-2-methanol (21.0 g), activated manganese dioxide (52.0 g) and tetrahydrofuran (800 ml) was stirred at 60° to 65° C. for 6 hours. After the insoluble portion was filtered off, the filtrate was concentrated; the residue was subjected to silica gel column chromatography. From the fraction eluted with ethyl acetate-chloroform (2:98, v/v), crystals of 6-(5-methyl-2-phenyl-4-oxazolylmethoxy) benzofuran-2-carbaldehyde (14.3 g, 69%) were obtained, which was then recrystallized from dichloromethane-isopropyl propyl ether to yield colorless prisms having a melting point of 137° to 138° C.

Reference Example 7

To a solution of (E)-ethyl 3-[6-(5-methyl-2-phenyl-4-oxazolylmethoxy)-2-benzofuranyl]acrylate (1.30 g) in tetrahydrofuran (50 ml), palladium-carbon (5%, 0.70 g) was added, followed by catalytic reduction at room temperature and under an atmospheric pressure of 1 atm. After the catalyst was filtered off, sodium borohydride (0.61 g) was added to the filtrate, followed by dropwise addition of methanol (10 ml) under refluxing conditions. After heating under refluxing conditions for 1 hour, the reaction mixture was poured over water and neutralized with 2N hydrochloric acid, followed by extraction with ethyl acetate. After the ethyl acetate layer was washed with water and dried (MgSO$_4$), the solvent was distilled off; the residue was subjected to silica gel column chromatography. From the fraction eluted with ethyl acetate-chloroform (1:5, v/v), 3-[6-(5-methyl-2-phenyl-4-oxazolylmethoxy)-2-benzofuranyl]propanol was obtained as an oily substance (0.90 g, 77%).

NMR (δ ppm, CDCl$_3$): 1.42 (1H, brs), 1.9–2.1 (2H, m), 2.44 (3H, s), 2.86 (2H, t, J=7.5 Hz), 3.74 (2H, t, J=6.5 Hz), 5.02 (2H, s), 6.34 (1H, s), 6.92 (1H, dd, J=8.5, 2 Hz), 7.11 (1H, d, J=2 Hz), 7.35 (1H, d, J=8.5 Hz), 7.4–7.5 (3H, m), 7.95–8.1 (2H, m)

Reference Example 8

A solution of diisobutylaluminum hydride in toluene (1M, 39 ml) was added dropwise to a solution of (E)-ethyl 3-[6-(5-methyl-2-phenyl-4-oxazolylmethoxy)-2-benzofuranyl] acrylate (5.23 g) in dichloromethane (200 ml) at 0° C. After stirring for 5 hours, methanol (3 ml)-water (10 ml) was carefully added to the reaction mixture. After the insoluble portion was filtered off, the filtrate was concentrated; the residue was subjected to silica gel column chromatography. From the fraction eluted with ethyl acetate-chloroform (1:5, v/v), crystals of (E)-3-[6-(5-methyl-2-phenyl-4-oxazolylmethoxy)-2-benzofuranyl]propen-1-ol (3.90 g, 83%) was obtained, which was then recrystallized from acetone-hexane to yield colorless prisms having a melting point of 143° to 144° C.

Reference Example 9

A mixture of (E)-3-[6-(5-methyl-2-phenyl-4-oxazolylmethoxy)-2-benzofuranyl]propen-1-ol (3.85 g), activated manganese dioxide (8.00 g) and dichloromethane (150 ml) was stirred at room temperature for 2 hours. After the insoluble portion was filtered off, the filtrate was concentrated to yield crystals of (E)-3-[6-(5-methyl-2-phenyl-4-oxazolylmethoxy)-2-benzofuranyl]acrolein (3.40 g, 89%), which was then recrystallized from dichloromethane-isopropyl ether to yield colorless prisms having a melting point of 132° to 133° C.

Reference Example 10

In the same manner as in Reference Example 1, 5-methoxysalicylaldehyde was reacted with methyl bromoacetate to yield methyl 2-formyl-4-methoxyphenoxyacetate (yield 86%), which was then recrystallized from acetone-hexane to yield colorless prisms having a melting point of 74° to 75° C.

Reference Example 11

In the same manner as in Reference Example 2, from methyl 2-formyl-4-methoxyphenoxyacetate, was obtained methyl 5-methoxybenzofuran-2-carboxylate (yield 71%), which was then recrystallized from ethyl acetate-hexane to yield colorless prisms having a melting point of 78° to 79° C.

Reference Example 12

In the same manner as in Reference Example 3, from methyl 5-methoxybenzofuran-2-carboxylate, was obtained methyl 5-hydroxybenzofuran-2-carboxylate (yield 89%), which was then recrystallized from acetone-isopropyl ether to yield colorless prisms having a melting point of 172° to 173° C.

Reference Example 13

In the same manner as in Reference Example 4, methyl 5-hydroxybenzofuran-2-carboxylate was reacted with 4-chloromethyl-5-methyl-2-phenyloxazole to yield methyl 5-(5-methyl-2-phenyl-4-oxazolylmethoxy)bezofuran-2-carboxylate (yield 87%), which was then recrystallized from acetone-ethyl acetate to yield colorless prisms having a melting point of 177° to 178° C.

Reference Example 14

In the same manner as in Reference Example 5, methyl 5-(5-methyl-2-phenyl-4-oxazolylmethoxy)bezofuran-2-carboxylate was reduced to yield 5-(5-methyl-2-phenyl-4-oxazolylmethoxy)bezofuran-2-methanol (yield 79%), which was then recrystallized from acetone-methanol to yield colorless prisms having a melting point of 162° to 163° C.

Reference Example 15

In the same manner as in Reference Example 6, 5-(5-methyl-2-phenyl-4-oxazolylmethoxy)bezofuran-2-methanol was oxidized to yield 5-(5-methyl-2-phenyl-4-oxazolylmethoxy)bezofuran-2-carbaldehyde (yield 42%), which was then recrystallized from acetone-methanol to yield light yellow prisms having a melting point of 137° to 138° C.

Reference Example 16

In the same manner as in Reference Example 11, (E)-ethyl 3-[5-(5-methyl-2-phenyl-4-oxazolylmethoxy)-2-benzofuranyl]acrylate was reduced with diisobutylaluminum hydride to yield (E)-3-[5-(5-methyl-2-phenyl-4-oxazolylmethoxy)-2-benzofuranyl]-2-propen-1-ol (yield 90%), which was then recrystallized from ethyl acetate-hexane to yield colorless prisms having a melting point of 145° to 146° C.

Reference Example 17

To a solution of (E)-3-[5-(5-methyl-2-phenyl-4-oxazolylmethoxy)-2-benzofuranyl]-2-propen-1-ol (2.00 g) in tetrahydrofuran (100 ml), palladium-carbon (5%, 0.30 g) was added, followed by catalytic reduction at room temperature and under an atmospheric pressure of 1 atm. After the catalyst was filtered off, the filtrate was concentrated to yield 3-[5-(5-methylphenyl-4-oxazolylmethoxy)-2-benzofuranyl]propanol (yield 93%), which was then recrys-tallized from acetone-isopropyl ether to yield colorless prisms having a melting point of 101° to 102° C.

What is claimed is:

1. A compound represented by the formula:

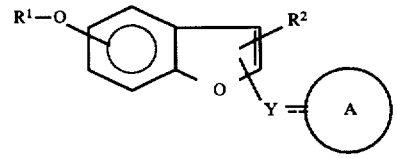

wherein

in which

..... represents a single or double bond, is a member selected from the group consisting of
1) a 5-membered heterocyclic group containing 1 to 4 atoms selected from N, O and S as ring component atoms;
2) a cyano group;
3) a carboxyl group;
4) a $C_{2-7}$ alkoxycarbonyl group;
5) a $C_{7-11}$ aryloxycarbonyl group;
6) a 5- or 6-membered heterocyclic-oxycarbonyl group containing 1 to 4 hetero atoms selected from N, O and S in addition to carbon atoms;
7) a sulfonic acid group;
8) a sulfamoyl group which is optionally mono-substituted by a $C_{1-4}$ alkyl group;
9) a phosphonic acid group;
10) a di-$C_{1-4}$ alkoxyphosphoryl group;
11) a carbamoyl group which is optionally mono-substituted by a $C_{1-4}$ alkyl group;
12) a $C_{2-7}$ alkylsulfonylthiocarbamoyl group; or
13) trifluoromethanesulfonamide;

$R^1$, which is attached to the oxygen atom through a $C_{1-8}$ divalent hydrocarbon chain, is a 5- or 6-membered ring or a condensed ring containing at least one nitrogen atom as a ring component atom which rings are unsubstituted or are substituted by
1) a hydrocarbon residue selected from aliphatic hydrocarbon residues, alicyclic hydrocarbon residues, alicyclic-aliphatic hydrocarbon residues, aromatic aliphatic hydrocarbon residues and aromatic hydrocarbon residues;
2) a 5- or 6-membered ring group containing as ring component atoms 1 to 3 atoms selected from N, O and S in addition to carbon atoms;
3) an amino group;
4) an N-mono-substituted amino group having one substituent selected from lower alkyl groups, cycloalkyl groups, aryl groups, aromatic heterocyclic groups, non-aromatic heterocyclic groups, aralkyl groups, acyl groups, carbamoyl groups, N-mono-substituted carbamoyl groups, N,N-di-substituted carbamoyl groups, lower alkoxycarbonyl groups, hydroxyl group, lower alkoxy groups and aralkyloxy groups;
5) an N,N-di-substituted amino group having two substituents, in which one substituent is the same as that for the above-mentioned N-mono-substituted amino groups and the other substituent is selected from lower alkyl groups, cycloalkyl groups, aryl groups and aralkyl groups; or those two substituents may form a cyclic amino group;

when the hydrocarbon residues 1) contain an alicyclic group, or when the 5- or 6-membered ring group 2) is saturated, it may have 1 to 3 lower alkyl groups;

when the hydrocarbon residue 1) contain an aromatic hydrocarbon group, or when the 5- or 6-membered ring group 2) is unsaturated, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups;

and when the 5- or 6-membered ring has two or more hydrocarbon residues as substituents therefor and the substituents are located at mutually adjacent positions on the ring, these residues may be linked together to form a saturated or unsaturated divalent chain hydrocarbon residue having 3 to 5 carbon atoms;

$R^2$ is (1) hydrogen, (2) halogen, (3) a hydrocarbon residue selected from aliphatic hydrocarbon residues, alicyclic hydrocarbon residues, alicyclic-aliphatic hydrocarbon residues, aromatic aliphatic hydrocarbon residues and aromatic hydrocarbon residues;

when the hydrocarbon residue contains an alicyclic group, it may have 1 to 3 lower alkyl groups; and when the hydrocarbon residue contains an aromatic hydrocarbon group, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups, (4) an optionally protected hydroxyl group, or (5) an optionally protected amino group;

Y represents a di- or tri-valent aliphatic hydrocarbon residue having 1 to 8 carbon atoms; and the benzene ring of the benzofuran moiety is unsubstituted or is substituted by 1 to 3 substituents selected from halogen, hydroxyl, cyano, nitro, trifluoromethyl, lower alkoxy groups, lower alkyl groups, lower alkoxycarbonyl groups, lower alkylthio groups and lower alkylamino groups;

or a pharmaceutically acceptable salt thereof.

2. A compound or salt thereof according to claim 1 wherein

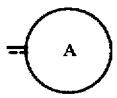

is a 5-membered heterocyclic group containing 1 to 4 atoms selected from N, O and S as ring component atoms.

3. A compound or salt thereof as defined in claim 1 wherein $R^1$ is a group represented by the formula

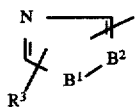

wherein $B^1$ represents a sulfur atom, an oxygen atom or $NR^4$ wherein $R^4$ represents a hydrogen atom, a lower alkyl group or an aralkyl group;

$B^2$ represents a nitrogen atom or $C—R^5$ wherein $R^5$ represents (1) a hydrogen atom, (2) a hydrocarbon residue selected from aliphatic hydrocarbon residues, alicyclic hydrocarbon residues, alicyclic-aliphatic hydrocarbon residues, aromatic aliphatic hydrocarbon residues and aromatic hydrocarbon residues;

when the hydrocarbon residue contains an alicyclic group, it may have 1 to 3 lower alkyl groups; and when the hydrocarbon residue contains an aromatic hydrocarbon group, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups, or (3) a 5- or 6-membered ring group containing as ring component atoms 1 to 3 atoms selected from N, O and S in addition to carbon atoms;

when the 5- or 6-membered ring group is saturated, it may have 1 to 3 lower alkyl groups; and when the 5- or 6-membered ring group is unsaturated, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups;

$R^3$ represents (1) a hydrogen atom, (2) a hydrocarbon residue selected from aliphatic hydrocarbon residues, alicyclic hydrocarbon residues, alicyclic-aliphatic hydrocarbon residues, aromatic aliphatic hydrocarbon residues and aromatic hydrocarbon residues;

when the hydrocarbon residue contains an alicyclic group, it may have 1 to 3 lower alkyl groups; and when the hydrocarbon residue contains an aromatic hydrocarbon group, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups, or (3) a 5- or 6-membered ring group containing as ring component atoms 1 to 3 atoms selected from N, O and S in addition to carbon atoms;

when the 5- or 6-membered ring group is saturated, it may have 1 to 3 lower alkyl groups; and when the 5- or 6-membered ring group is unsaturated, it may have 1 to 4 substituents selected from halogen, hydroxy, cyano, nitro, trifluoromethyl, lower alkoxy groups, lower alkyl groups, lower alkoxycarbonyl groups, lower alkylthio groups and lower alkylamino groups; and when $R^3$ and $R^5$ are attached to adjacent carbon atoms $R^3$ and $R^5$ may be linked to form a condensed ring.

4. A compound or salt thereof according to claim 1 wherein

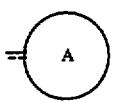

is a member selected from the group consisting of

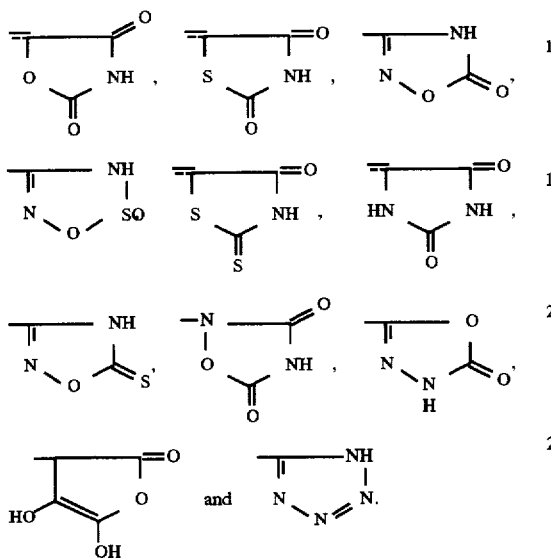

5. A compound or salt thereof according to claim 1, wherein

=(A) is [triazole structure]

6. A compound or salt thereof according to claim 1, wherein

=(A) is [O-NH-C(=O) ring structure]

7. A compound or salt thereof according to claim 1, wherein

=(A) is [S-NH-C(=O) ring structure]

8. A compound or salt thereof according to claim 1, wherein $R^2$ is hydrogen.

9. A compound or salt thereof according to claim 1, wherein Y is —$CH_2CH_2CH_2$—.

10. A compound or salt thereof according to claim 1, wherein $R^1$ is a oxazole group which is optionally substituted by phenyl and/or methyl, and which is attached through a methylene group; the partial formula =(A) represents

[structures: triazole, O-NH oxazolidinone, S-NH thiazolidinone]

$R^2$ is hydrogen;

Y is di- or tri-valent aliphatic hydrocarbon residue having 1 to 4 carbon atoms; $R^1$-0 is attached to the 6-position and Y is attached to the 2-position on the benzofuran ring.

11. A compound according to claim 1, which is

5-[2-[6-(5-methyl-2-phenyl-4-oxazolylmethoxy)-2-benzofuranyl]ethyl]-1H-tetrazole, 5-[3-[6-(5-methyl-2-phenyl-4-oxazolylmethoxy)-2-benzofuranyl]propyl]-1H-tetrazole, 5-[4-[6-(5-methyl-2-phenyl-4-oxazolylmethoxy)-2-benzofuranyl]butyl]-1H-tetrazole, 5-[6-(5-methyl-2-phenyl-4-oxazolylmethoxy)-2-benzofuranylmethylidene]-2,4-thiazolidinedione, 5-[6-(5-methyl-2-phenyl-4-oxazolylmethoxy)-2-benzofuranylmethyl]-2,4-thiazolidinedione, 5-[3-[6-(5-methyl-2-phenyl-4-oxazolylmethoxy)-2-benzofuranyl]propyl]-2,4-thiazolidinedione, 5-[6-(5-methyl-2-phenyl-4-oxazolylmethoxy)-2-benzofuranylmethyl]-2,4-oxazolidinedione, 5-[3-[6-(5-methyl-2-phenyl-4-oxazolylmethoxy)-2-benzofuranyl]propyl]-2,4-oxazolidinedione or 5-[3-[5-(5-methyl-2-phenyl-4-oxazolylmethoxy)-2-benzofuranyl]propyl]-1H-tetrazole.

12. A pharmaceutical composition comprising a pharmaceutically effective amount of a compound as defined in claim 1 or a pharmaceutically acceptable salt thereof and a pharmaceutically acceptable carrier therefor.

13. A pharmaceutical composition according to claim 12, which is for treating diabetes.

14. A pharmaceutical composition according to claim 12, which is for enhancing insulin sensitivity.

15. A pharmaceutical composition according to claim 12, which is for treating hyperlipidemia.

16. Method for treating diabetes in a mammal in need thereof, which comprises administering to such mammal a therapeutically effective amount of a compound as defined in claim 1 or a pharmaceutically acceptable salt thereof.

17. Method for treating hyperlipidemia in a mammal in need thereof, which comprises administering to such mammal a therapeutically effective amount of a compound as defined in claim 1 or a pharmaceutically acceptable salt thereof.

* * * * *